United States Patent
DeLuca et al.

(10) Patent No.: US 8,642,579 B2
(45) Date of Patent: Feb. 4, 2014

(54) 1-DESOXY-2-METHYLENE-19-NOR-VITAMIN D ANALOGS AND THEIR USES

(75) Inventors: Hector F. DeLuca, Deerfield, WI (US); Katarzyna M. Barycka, Madison, WI (US); Izabela Sibilska, Warsaw (PL); Lori A. Plum, Arena, WI (US); Margaret Clagett-Dame, Deerfield, WI (US); Rafal Barycki, Madison, WI (US); Rafal R. Sicinski, Warsaw (PL); Katarzyna Plonska-Ocypa, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 75 days.

(21) Appl. No.: 12/895,478

(22) Filed: Sep. 30, 2010

(65) Prior Publication Data

US 2011/0082121 A1    Apr. 7, 2011

Related U.S. Application Data

(60) Provisional application No. 61/248,125, filed on Oct. 2, 2009.

(51) Int. Cl.
*A61K 31/59* (2006.01)
*C07C 401/00* (2006.01)

(52) U.S. Cl.
USPC .......................... 514/167; 552/653

(58) Field of Classification Search
USPC ........................ 514/167; 552/653
See application file for complete search history.

(56) References Cited

U.S. PATENT DOCUMENTS

| | | | |
|---|---|---|---|
| 3,565,924 A | 2/1971 | DeLuca et al. | |
| 4,248,791 A | 2/1981 | DeLuca et al. | |
| 4,269,777 A | 5/1981 | DeLuca et al. | |
| 4,292,249 A | 9/1981 | Nishikawa et al. | |
| 4,424,161 A | 1/1984 | Holick | |
| 4,500,460 A | 2/1985 | DeLuca et al. | |
| 6,392,071 B1 | 5/2002 | DeLuca et al. | |
| 8,455,467 B2 * | 6/2013 | DeLuca et al. | 514/167 |
| 2005/0101576 A1 * | 5/2005 | Whitehouse et al. | 514/167 |
| 2010/0196308 A1 * | 8/2010 | Jimenez et al. | 424/85.1 |
| 2011/0052707 A1 * | 3/2011 | Buck et al. | 424/490 |

FOREIGN PATENT DOCUMENTS

WO    98/41501    9/1998

OTHER PUBLICATIONS

Urushino, N. et al., "Kinetic studies of 25-hydroxy-19-nor-vitamin D3 and 1alpha,25-dihydroxy-19-nor-vitamin D3 hydroxylation by CYP27B1 and CYP 24A1", Drug Metabolism and Disposition 200709 US LNKd-DOI: 10.1124/DMD.107.015602, vol. 35, No. 9, pp. 1482-1488, 2007.

Sibilska, I. et al, "1-Desoxy-analog of 2MD: Synthesis and biological activity of (20S)-25-hydroxy-2-methylene-19-norvitamin D3", Journal of Steroid Biochemistry and Molecular Biology, vol. 121, No. 1-2, pp. 51-55, 2010.

The Merck Index—an Encyclopedia of Chemicals, Drugs, and Biologicals, Eleventh Edition, pp. 1578-1579, 1989.

International Search Report/Written Opinion, PCT International Application No. PCT/US2010/050977, mailed Apr. 27, 2011.

* cited by examiner

*Primary Examiner* — Sabiha N Qazi
(74) *Attorney, Agent, or Firm* — Andrus Intellectual Property Law, LLP

(57) ABSTRACT

This invention discloses 1-desoxy-2-methylene-19-nor-vitamin D analogs, and specifically (20S)-25-hydroxy-1-desoxy-2-methylene-19-nor-vitamin $D_3$ and pharmaceutical uses therefor. This compound exhibits relatively high binding activity and pronounced activity in arresting the proliferation of undifferentiated cells and inducing their differentiation to the monocyte thus evidencing use as an anti-cancer agent especially for the treatment or prevention of leukemia, colon cancer, breast cancer, skin cancer or prostate cancer.

31 Claims, 7 Drawing Sheets

Competitive VDR Binding

■ 1,25(OH)$_2$D$_3$
○ 1-desoxy-2MD $K_i$:  1,25(OH)$_2$D$_3$ = 5 x 10$^{-11}$ M
1-desoxy-2MD = 1 x 10$^{-10}$ M

1-DESOXY-2-METHYLENE-19-NOR-VITAMIN D ANALOGS AND THEIR USES

BACKGROUND OF THE INVENTION

This invention relates to vitamin D compounds, and more particularly to 1-Desoxy-2-Methylene-19-Nor-Vitamin D analogs and their pharmaceutical uses, and especially (20S)-25-hydroxy-1-desoxy-2-methylene-19-norvitamin $D_3$, its biological activities, and its pharmaceutical uses.

The natural hormone, $1\alpha,25$-dihydroxyvitamin $D_3$ and its analog in the ergosterol series, i.e. $1\alpha,25$-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of $1\alpha,25$-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of $1\alpha,25$-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of $1\alpha,25$-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et at U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. $1\alpha$-hydroxy-2-methylene-19-nor-pregnacalciferol is described in U.S. Pat. No. 6,566,352 while $1\alpha$-hydroxy-2-methylene-19-nor-homopregnacalciferol is described in U.S. Pat. No. 6,579,861 and $1\alpha$-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to $1\alpha,25$-dihydroxyvitamin $D_3$. Their biological activities make these compounds excellent candidates for a variety of pharmaceutical uses, as set forth in the '352, '861 and '622 patents.

Analogs of the natural hormone $1\alpha,25$-dihydroxyvitamin $D_3$ characterized by the transposition of the A-ring exocyclic methylene group from carbon 10 (C-10) to carbon 2 (C-2) (e.g., $1\alpha,25$-dihydroxy-2-methylene-19-norvitamin D analogs) have been synthesized and tested [see Sicinski et al., J. Med. Chem., 41, 4662 (1998); Sicinski et al., Steroids 67, 247 (2002); and, DeLuca et al., U.S. Pat. Nos. 5,843,928; 5,936,133 and 6,382,071)]. Molecular mechanics studies performed on these analogs predict that a change of A-ring conformation may cause flattening of the cyclohexanediol ring. Molecular mechanics calculations and NMR studies also predict that the A-ring conformational equilibrium would be ca. 6:4 in favor of the conformer having an equatorial $1\alpha$-OH. It was further predicted that introduction of the 2-methylene group into 19-nor-vitamin D carbon skeleton would change the character of its $1\alpha$- and $3\beta$-A-ring hydroxyls. They would both be in allylic positions similar to the $1\alpha$-hydroxyl group in the molecule of the natural hormone [i.e., $1\alpha,25$-$(OH)_2D_3$]. It was found that $1\alpha,25$-dihydroxy-2-methylene-19-norvitamin D analogs are characterized by significant biological potency. In addition, the biological potency of such analogs may be enhanced dramatically where "unnatural" (20S)-configuration is present. Taking into account these findings, the present invention is aimed at vitamin D compounds characterized by the transposition of the A-ring exocyclic methylene group from carbon 10 (C-10) to carbon 2 (C-2) (e.g., 2-methylene-19-norvitamin D analogs). Although these analogs lack $1\alpha$-OH, that is important for biological activity, such hydroxyl group can be potentially introduced enzymatically in the living organisms.

SUMMARY OF THE INVENTION

The present invention is directed toward 1-desoxy-2-methylene-19-nor-vitamin D analogs, and their pharmaceutical uses, and more specifically toward (20S)-25-hydroxy-1-desoxy-2-methylene-19-norvitamin $D_3$, its biological activity, and various pharmaceutical uses for this compound.

Structurally these 1-desoxy-2-methylene-19-nor-vitamin D analogs are characterized by the general formula I shown below:

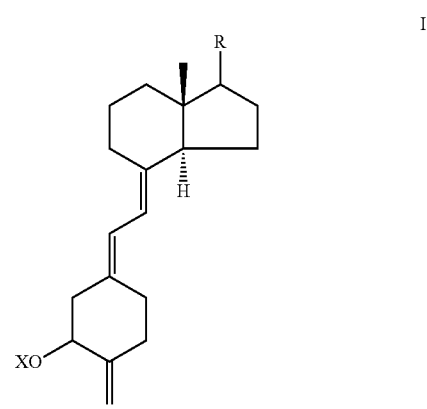

where X is selected from the group consisting of hydrogen and a hydroxy-protecting group, and where the group R represents any of the typical side chains known for vitamin D type compounds. Thus, R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

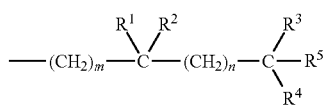

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH—groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

Specific important examples of side chains with natural 20R-configuration are the structures represented by formulas (a), (b), (c), (d) and (e) below, i.e., the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e).

(a)
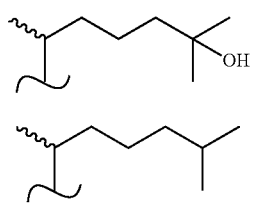

(b)

(c)
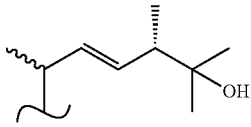

(d)
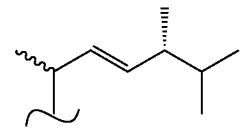

(e)
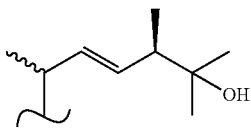

The wavy line to the carbon 20 indicates that carbon 20 may have either the R or S configuration.

The preferred analog is (20S)-25-hydroxy-1-desoxy-2-methylene-19-norvitamin D$_3$ which has the following formula Ia:

Ia
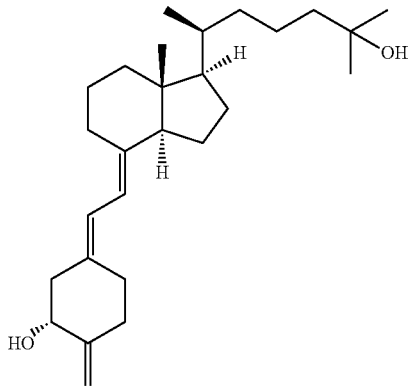

The above compounds of formula I, especially formula Ia, exhibit a desired, and highly advantageous, pattern of biological activity. These compounds are characterized by relatively high binding to vitamin D receptors, i.e. they bind with only slightly lower affinity than 1α,25-dihydroxyvitamin D$_3$. They are only slightly less potent causing differentiation of HL-60 cells than 1,25(OH)$_2$D$_3$. They also exhibit relatively low transcriptional activity as well as relatively low activity in their ability to mobilize calcium from bone, and in their ability to promote intestinal calcium transport, as compared to 1α,25-dihydroxyvitamin D$_3$. Hence, these compounds can be characterized as having relatively little calcemic activity.

The above compounds I, and particularly Ia, have relatively high binding affinity, are characterized by relatively high cell differentiation activity, but have notably lower calcemic activities. Thus, these compounds have potential as anti-cancer agents and provide therapeutic agents for the prevention or treatment of leukemia, colon cancer, breast cancer, skin cancer and prostate cancer.

One or more of the compounds may be present in a composition to treat or prevent the above-noted diseases in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually, or parenterally in dosages of from about 0.01 µg/day to about 1000 µg/day, preferably from about 0.1 µg/day to about 500 µg/day.

BRIEF DESCRIPTION OF THE DRAWINGS

FIGS. 1-5 illustrate various biological activities of (20S)-25-hydroxy-1-desoxy-2-methylene-19-norvitamin $D_3$, hereinafter referred to as "1-desoxy-2MD," as compared to the native hormone 1α,25-dihydroxyvitamin $D_3$, hereinafter "1,25(OH)$_2$D$_3$."

FIG. 1 is a graph illustrating the relative activity of 1-desoxy-2MD and 1,25(OH)$_2$D$_3$ to compete for binding with [$^3$H]-1,25-(OH)$_2$-D$_3$ to the full-length recombinant rat vitamin D receptor;

FIG. 2 is a graph illustrating the percent HL-60 cell differentiation as a function of the concentration of 1-desoxy-2MD and 1,25(OH)$_2$D$_3$;

FIG. 3 is a graph illustrating the in vitro transcription activity of 1,25(OH)$_2$D$_3$ as compared to 1-desoxy-2MD;

DETAILED DESCRIPTION OF THE INVENTION

Figure 1:
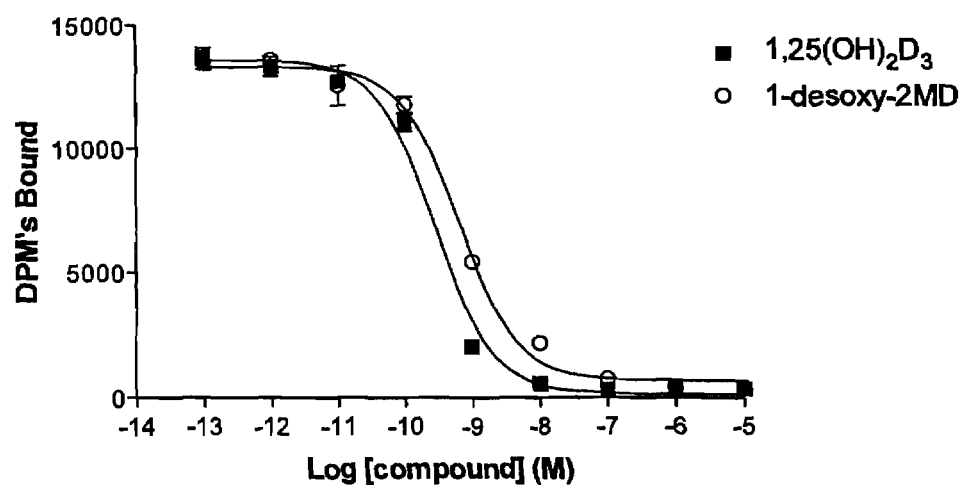

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

The preparation of 2-methylene-19-norvitamin D analogs of the basic structure I can be accomplished by a common general method, i.e., the condensation of a bicyclic Windaus-Grundmann type ketone II with the allylic phosphine oxide III:

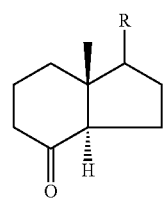

II

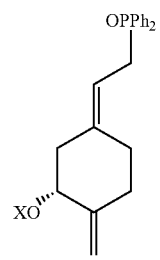

III

In the structures II and III, groups X and R represent groups defined above; X being preferably hydroxy-protecting group, it being also understood that any functionalities in R that might be sensitive, or that interfere with the condensation reaction, be suitable protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713)].

Hydrindanones of the general structure II are known, or can be prepared by known methods. Specific important examples of such known bicyclic ketones are the structures with the side chains (a), (b), (c) and (d) described above, i.e., 25-hydroxy Grundmann's ketone (e) [Baggiolini et al., J. Org. Chem, 51, 3098 (1986)]; Grundmann's ketone (f) [Inhoffen et al., Chem. Ber., 90, 664 (1957)]; 25-hydroxy Windaus ketone (g) [Baggiolini et al., J. Org. Chem., 51, 3098 (1986)] and Windaus ketone (h) [Windaus et al., Ann., 524, 297 (1936)]:

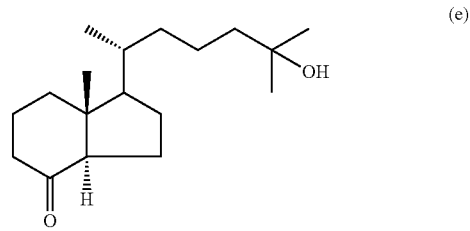

(e)

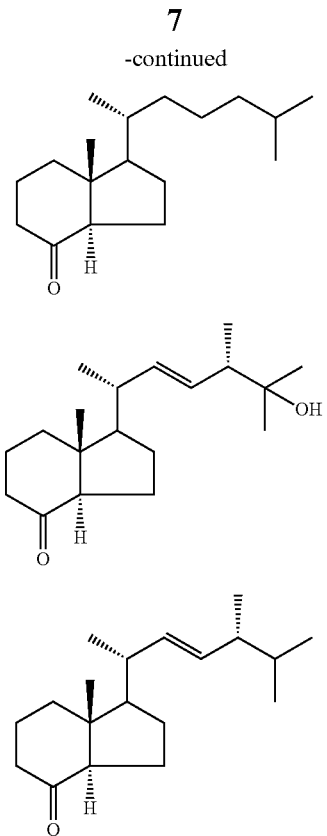

Regarding the preparation of the phosphine oxides of the structure III, alternative synthetic routes were established. As set forth in SCHEME I, an achiral, commercially available acetal-ketone 1, was enantioselectively hydroxylated to the hydroxy ketone 2, using the method elaborated by Hayashi et al. [J. Org. Chem. 69, 5966 (2004)] and involving the reaction of a ketone with nitrosobenzene in the presence of a catalytic amount of L-proline. The introduced secondary hydroxyl was silylated and the protected compound 3 was subjected to the Wittig reaction with an ylide generated from methyltriphenylphosphonium bromide and n-butyllithium. In the resulting olefinic compound 4 the carbonyl group was deprotected in the reaction with the Lewis acid (FeCl$_3$) and the formed cyclohexanone 5 was subjected to a Peterson reaction leading to the mixture of α,β-unsaturated esters 6 and 7. Although possible at this stage, the separation of the geometric isomers was more easily achieved (by column chromatography) after the reduction step, providing the E- and Z-allylic alcohols 8 and 9, respectively. The E-isomer 8 was next transformed in the three-step procedure into the corresponding phosphine oxide 10. Wittig-Horner coupling of the known Grundmann ketone 11 [see Sicinski et al., J. Med. Chem., 41, 4662 (1998)] with the lithium phosphinoxy carbanion generated from the phosphine oxide 10 was subsequently carried out, producing the protected 19-norvitamin D compound, which after hydroxyls deprotection with tetrabutylammonium fluoride provided the desired (20S)-2-methylene-25-hydroxy-19-nor-vitamin D$_3$ (12, 1-desoxy-2MD). This synthetic path is described in EXAMPLE I herein and the alternative method of the synthesis of the A-ring fragment, the phoshine oxide 27, and its coupling with the ketone 11 is described in EXAMPLE II herein.

SCHEME II shows this different synthetic sequence leading to the building block 27 and to the final vitamin 12. As a chiral starting compound served a commercially available D-(−)-quinic acid 13, which was at first converted to the known lactone 14. Treatment of this compound with a 1,1'-thiocarbonyldiimidazole resulted in formation of the cyclic thiocarbonate 15 [see Mills et al., Tetrahedron Lett. 29, 281 (1988)]. The Barton-McCombie deoxygenation reaction of the thiocarbonate 15 with tributyltin hydride and AIBN provided two isomeric products: the known compound 16 [see Gonzales-Bello et al., J. Chem. Soc., Perkin Trans. 1, 849 (1999)] and the desired diol 17. Oxidation of the secondary hydroxyl in the latter isomer yielded the ketone 18 which was subjected to the Wittig methylenation. The lactone ring in the formed compound 19 was then opened and the secondary hydroxyl silylated. The methyl ester moiety in the obtained product 20 was reduced and the diol 21 was subjected to periodate oxidation. Wittig reaction of the obtained cyclohexanone 22 with methyl(triphenylphosphoranylidene)acetate provided the mixture of α,β-unsaturated esters 23 and 24. They were reduced with DIBALH and the obtained allylic alcohols separated by column chromatography. The E-isomer 25 was then converted into the corresponding allylic phosphine oxide 27. Its anion, generated by phenyllitium, was coupled with the Grundmann ketone 11 and the final 19-norvitamin 12 (1-desoxy-2MD) was obtained after acidic hydroxyl deprotection.

As it is evident from EXAMPLE I and II, other 19-norvitamin D analogs having the different side-chains may be synthesized by the methods set forth herein.

This invention is described by the following illustrative examples. In these examples specific products identified by Arabic numerals (e.g., 1, 2, 3, etc) refer to the specific structures so identified in the preceding description and in the SCHEME I and SCHEME II.

EXAMPLES

Chemistry. Melting points (uncorrected) were determined on a Thomas-Hoover capillary melting-point apparatus. Optical rotations were measured in chloroform using a Perkin-Elmer 241 automatic polarimeter at 22° C. Ultraviolet (UV) absorption spectra were recorded with a Perkin-Elmer Lambda 3B UV-VIS spectrophotometer in ethanol. $^1$H nuclear magnetic resonance (NMR) spectra were recorded in deuteriochloroform at 200, 400 and 500 MHz with a Varian Unity, Bruker DMX-400 and Bruker DMX-500 spectrometers, respectively. $^{13}$C nuclear magnetic resonance (NMR) spectra were recorded at 50, 100 and 125 MHz with the same spectrometers in deuteriochloroform. Chemical shifts (δ) were reported downfield from internal Me$_4$Si (δ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example I

Preparation of (20S)-2-methylene-25-hydroxy-19-nor-vitamin D$_3$ (12, 1-desoxy-2MD) from the phosphine oxide 10

(a) α-Hydroxylation of a ketal-ketone 1 (SCHEME I). (R)-7-Hydroxy-1,4-dioxa-spiro[4.5]decan-8-one (2). To a stirred solution of 1,4-cyclohexanedione monoethylene ketal (1; 3.00 g, 19.23 mmol) and L-proline (0.97 g, 8.42 mmol) in CHCl$_3$ (10 mL), a solution of nitrosobenzene (3.60 g, 33.65 mmol) in CHCl$_3$ (16 mL) was slowly added at 4° C. over 24 h by a syringe pump. Then the mixture was stirred at room temperature for additional 2 h. Reaction was quenched with brine, and the organic materials were extracted with ethyl acetate, dried (MgSO$_4$) and concentrated in vacuum. Purification by column chromatography on silica (0.5→20% ethyl acetate/hexane gradient) gave an oily α-hydroxy ketone 2 (1.45 g, 44%). Purity of the product was checked by HPLC (4.6 mm×25 cm Chiralcell OD-H column, 1.5 mL/min) using hexane/2-propanol (99:1) solvent system: it was found to have enantiomeric excess (ee) higher than 94% (R$_V$=5.7 mL; for the S-enantiomer R$_V$=4.7 mL).

2: [α]$_D$+27° (c 0.65, CHCl$_3$); $^1$H NMR (200 MHz, CDCl$_3$) δ 1.85 (1H, t, J=12.4 Hz, 6β-H), 2.05 (2H, m, 10-H$_2$), 2.50 (br m, 6α- and 9β-H), 2.70 (1H, dt, J=6.8, 13.2 Hz, 9α-H), 3.46 (1H, s, OH), 4.03 (4H, m, O—CH$_2$CH$_2$—O), 4.38 (1H, dd, J=12.4, 6.8 Hz, 7α-H); HRMS (ESI) exact mass calculated for C$_8$H$_{12}$O$_4$Na (M$^+$+Na) 195.0633, found 195.0628.

(b) Protection of α-hydroxy ketone 2. (R)-7-[(tert-Butyldiphenylsilyl)oxy]-1,4-dioxa-spiro[4.5]decan-8-one (3). tert-Butyldiphenylsilyl chloride (3.55 mL, 3.75 g, 13.65 mmol) was added to a solution of α-hydroxy ketone 2 (1.60 g, 13.65 mmol) and imidazole (2.32 g, 33.9 mmol) in anhydrous DMF (9 mL). The mixture was stirred at room temperature for 18 h. The reaction was quenched with brine and extracted with hexane. The combined organic phases were dried (MgSO$_4$) and concentrated under reduced pressure. Column chromatography on silica (1→4% hexane/ethyl acetate gradient) provided the protected compound 3 (3.35 g, 88%) as a colorless oil.

3: $^1$H NMR (200 MHz, CDCl$_3$) δ 1.10 (9H, s, Si-t-Bu), 1.8-2.1 (4H, br m, 6- and 10-H$_2$), 2.35 (2H, m, 9-H$_2$), 3.62 (1H, m, one of —O—CH$_2$CH$_2$—O—), 3.82 (3H, m, three of —O—CH$_2$CH$_2$—O—), 4.40 (1H, dd, J=11.8, 7.6 Hz, 7α-H), 7.38 (6H, m, Ar—H), 7.67 (4H, m, Ar—H); $^{13}$C NMR (50 MHz, CDCl$_3$) δ 19.4, 27.1, 34.7, 35.9, 43.8, 64.5, 64.7, 73.8, 107.6, 127.8, 129.9, 133.3, 134.1, 136.0, 207.7; HRMS (ESI) exact mass calculated for C$_{24}$H$_{30}$O$_4$SiNa (M$^+$+Na) 433.1811, found 433.1800.

(c) Wittig reaction of the ketone 3. (R)-7-[(tert-Butyldiphenylsilyl)oxy]-8-methylene-1,4-dioxa-spiro[4.5]decane (4). To methyltriphenylphosphonium bromide (2.5 g, 6.99 mmol) in anhydrous THF (20 mL) at 0° C. was added dropwise n-BuLi (1.6 M in hexanes; 8.8 mL, 14.08 mmol). After 15 min another portion of phosphonium salt (2.5 g, 6.99 mmol) was added, and the solution was stirred at 0° C. for 10 min, and at room temperature for 20 min. The orange-red mixture was then cooled to −78° C. and siphoned to the precooled (−78° C.) solution of the ketone 3 (2.85 g, 6.93 mmol) in anhydrous THF (7 mL). The reaction mixture was stirred at −78° C. for 4 h and then at room temperature for 1 h. The mixture was poured into brine and extracted with hexane. Organic extracts were dried (MgSO$_4$), and evaporated to give an orange oily residue which was purified by flash chromatography on silica. Elution with hexane/ethyl acetate (97:3) gave pure 4-methylene compound 4 (2.62 g, 93%) as a colorless oil.

4: $^1$H NMR (200 MHz, CDCl$_3$) δ 1.01 (9H, s, Si-t-Bu), 1.43 (2H, m, 10-H$_2$), 1.62 (2H, m, 6-H$_2$), 2.19 (2H, m, 9-H$_2$), 3.36 (1H, m, one of O—CH$_2$CH$_2$—O), 3.73 (3H, m, three of O—CH$_2$CH$_2$—O), 4.30 (1H, dd, J=11.0, 5.0 Hz, 7α-H), 4.88 and 5.31 (1H and 1H, each br s, =CH$_2$), 7.35 (6H, m, Ar—H), 7.70 (4H, m, Ar—H); $^{13}$C NMR (50 MHz, CDCl$_3$) δ 14.5, 19.5, 22.9, 30.0, 31.8, 36.3, 44.5, 64.1, 64.3, 71.2, 106.6, 109.2, 127.7, 129.8, 134.1, 134.8, 135.9, 136.2, 149.3; HRMS (ESI) exact mass calcd for C$_{25}$H$_{32}$O$_3$SiNa (M$^+$+Na) 431.2019, measured 431.2028.

(d) Deprotection of a carbonyl group in the ketal 4. (R)-3-[(tert-Butyldiphenylsilyl)oxy]-4-methylene-cyclohexanone (5). To a solution of ketal 4 (160 mg, 0.392 mmol) in methylene chloride (11 mL) at room temperature FeCl$_3$×6H$_2$O (547 mg, 2.02 mmol) was added. The resulting dark yellow suspension was stirred for 50 min and quenched by the addition of water. The aqueous layer was extracted with methylene chloride, the combined organic layers were dried (MgSO$_4$) and concentrated under reduced pressure. Column chromatography on silica of the resulting yellow residue using hexane/ethyl acetate (95:5) yielded ketone 5 (141 mg, 99%) as a colorless oil.

5: $^1$H NMR (500 MHz, CDCl$_3$): δ 1.05 (9H, s, Si-t-Bu), 2.32-2.52 (5H, br m, 2β-H, 5-H$_2$ and 6-H$_2$), 2.83 (1H, m, 2α-H), 4.47 (1H, br t, J~6 Hz, 3α-H), 4.90 (2H, s, =CH$_2$), 7.40 (6H, m, Ar—H), 7.65 (4H, m, Ar—H); $^{13}$C NMR (125 MHz, CDCl$_3$) δ 19.6, 27.1, 32.8, 36.9, 44.8, 72.8, 107.1, 108.2, 128.0, 129.8, 133.0, 133.3, 135.1, 207.7; HRMS (ESI) exact mass calculated for C$_{23}$H$_{28}$O$_2$SiNa (M$^+$+Na) 387.1757, found 387.1746.

(e) Peterson reaction of the ketone 5. [(R)-3'-[(tert-Butyldiphenylsilyl)oxy]-4'-methylene-cyclohexylidene]acetic acid methyl ester (mixture of 6 and 7). To a solution of diisopropylamine (48.5 μL, 376 μmol) in anhydrous THF (260 μL) was added n-BuLi (2.5 M in hexanes; 148 μL, 367 μmol) under argon at −78° C. with stirring, and methyl(trimethylsilyl)acetate (60 μL, 367 μmol) was then added. After 15 minutes keto compound 5 (63 mg, 172.8 μmol) in anhydrous THF (300 μL+80 μL) was added dropwise. The solution was stirred at −78° C. for 2 hours, and the reaction was quenched with saturated NH$_4$Cl, poured into brine and extracted with ethyl acetate. The combined organic extracts were dried (MgSO$_4$) and evaporated. The residue was dissolved in hexane and applied on a silica Sep-Pak cartridge. Elution with hexane/ethyl acetate (98:2) gave unsaturated esters 6 and 7 (65 mg, 90%) as a colorless oil.

6 and 7 (mixture of isomers): $^1$H NMR (200 MHz, CDCl$_3$; selected signals) δ 1.15 and 1.17 (5H and 4H, each s, 2×Si-t-Bu), 2.1-3.3 (6H, br m, 2'-, 5'- and 6'-H$_2$), 3.69 and 3.73 (1.67H and 1.33H, each s, 2×COOCH$_3$), 4.29 (1H, m, 3'α-H), 4.82, 4.90, 4.93, 5.12 (0.56H, 0.56H, 0.44H and 0.44H, each br s, =CH$_2$), 5.48 and 5.83 (0.44H and 0.56H, each br s, C H—COOMe), 7.45 (6H, m, Ar—H), 7.75 (4H, m, Ar—H); HRMS (ESI) exact mass calculated for C$_{26}$H$_{32}$O$_3$SiNa (M$^+$+Na) 443.2019, found 443.2035.

(f) Reduction of the esters 6 and 7. (E)- and (Z)-2-[(R)-3'-[(tert-Butyldiphenylsilyl)oxy]-4'-methylene-cyclohexylidene]ethanols (8 and 9). Diisobutylaluminium hydride (1.5 M in toluene; 1.9 mL, 2.85 mmol) was slowly added to a stirred solution of allylic esters 6 and 7 (165 mg, 0.392 mmol) in toluene:methylene chloride (2:1; 8 mL) at −78° C. under argon. Stirring was continued at −78° C. for 1 h and at −40° C. for 30 min. The mixture was quenched by slow addition of potassium-sodium tartate (2N, 4 mL), aqueous HCl (2N, 4 mL) and H$_2$O (14 mL), and extracted with ethyl acetate. Combined organic layers were washed with brine, dried (MgSO$_4$) and evaporated. The residue was passed through a silica Sep-Pak cartridge with hexane/ethyl acetate (9:1). The obtained mixture of allylic alcohols was separated by HPLC (9.4 mm×25 cm Zorbax-Sil column, 4 mL/min) using hexane/ethyl acetate (8:2) solvent system: the Z-isomer 9 (82 mg, 53%) was collected at R$_V$=35 mL and the E-isomer 8 (60 mg, 39%) at R$_V$=41 mL.

8 (minor E-isomer): $^1$H NMR (500 MHz, CDCl$_3$) δ 1.08 (9H, s, Si-t-Bu), 1.96 (1H, ~dt, J~5, 12.5 Hz, 6'β-H), 2.07

(1H, dd, J=12.5, 8.5 Hz, 2'β-H), 2.08 (1H, m, 5'α-H), 2.13 (1H, dd, J=12.5, 4.5 Hz, 2'α-H), 2.31 (1H, dt, J=12.5, 4.5 Hz, 6'α-H), 2.48 (1H, dt, J=12.5, 5.5 Hz, 5'β-H), 4.09 (2H, d, J=7.0 Hz, —CH$_2$OH), 4.14 (1H, dd, J=8.5, 4.5 Hz, 3'α-H), 4.82 and 5.10 (1H and 1H, each br s, =CH$_2$), 5.16 (1H, t, J=7.5 Hz, 2-H), 7.39 (6H, m, Ar—H), 7.65 (4H, m, Ar—H); $^{13}$C NMR (125 MHz, CDCl$_3$) δ 19.3, 27.0, 29.3, 32.7, 46.6, 58.7, 74.0, 107.2, 123.6, 127.5, 129.6, 133.8, 134.5, 135.8, 139.7, 149.6; HRMS (ESI) exact mass calculated for C$_{25}$H$_{32}$O$_2$SiNa (M$^+$+Na) 415.2070, found 415.2059.

9 (major Z-isomer): $^1$H NMR (500 MHz, CDCl$_3$) δ 1.09 (9H, s, Si-t-Bu), 1.99 (2H, m, 2'β- and 5'α-H), 2.11 (2H, m, 6'α- and 6'β-H), 2.25 (1H, dd, J=13.0, 4.5 Hz, 2'α-H), 2.48 (1H, dt, J=12.5, 5.5 Hz, 5'β-H), 3.62 (1H, dd, J=10.0, 7.2 Hz, one of —CH$_2$OH), 3.71 (1H, dd, J=10.0, 7.0 Hz, one of —CH$_2$OH), 4.09 (1H, dd, J=9.0, 4.5 Hz, 3'α-H), 4.82 and 5.10 (1H and 1H, each br s, =CH$_2$), 5.37 (1H, t, J=7.0 Hz, 2-H), 7.39 (6H, m, Ar—H), 7.65 (4H, m, Ar—H); $^{13}$C NMR (125 MHz, CDCl$_3$) δ 19.3, 27.0, 33.4, 37.3, 38.8, 58.3, 73.7, 107.1, 123.6, 127.6, 129.7, 133.7, 134.5, 135.8, 139.4, 149.6; HRMS (ESI) exact mass calculated for C$_{25}$H$_{32}$O$_2$SiNa (M$^+$+Na) 415.2070, found 415.2067.

(g) Preparation of the phosphine oxide 10. [2-[(Z)—(R)-3'-[(tert-Butyldiphenylsilyl)oxy]-4'-methylene-cyclohexylidene]ethyl]diphenyl phosphine oxide (10). To a solution of an allylic alcohol 8 (49 mg, 125 µmol) in anhydrous THF (1.2 mL) was added n-BuLi (2.5 M in hexanes; 50 µl, 125 µmol) under argon at 0° C. A solution of a freshly recrystallized tosyl chloride (24 mg, 125 µmol) in anhydrous THF (230 µL) was then added to the allylic alcohol—n-BuLi solution. The mixture was stirred at 0° C. for 5 min and set aside at 0° C. In another dry flask with air replaced by argon, n-BuLi (2.5 M in hexanes; 1 mL, 0.25 mmol) was added to a solution of Ph$_2$PH (44.2 µl, 254 µmol) in anhydrous THF (360 µL) at 0° C. with stirring. The red solution was siphoned under argon pressure to the solution of tosylate until the orange color persisted (ca. one-half of the solution was added). The resulting mixture was stirred for an additional 30 min at 0° C. and quenched by addition of H$_2$O (14 µL). Solvents were evaporated under reduced pressure, the residue was redissolved in methylene chloride (1.2 mL), and stirred with 10% H$_2$O$_2$ (0.9 mL) at 0° C. for 1 h. The organic layer was separated, washed with cold aqueous sodium sulfite and water, dried (MgSO$_4$), and evaporated. The residue was subjected to flash chromatography on silica. Elution with hexane/ethyl acetate (6:4) gave the phosphine oxide 10 (64 mg, 79%).

10: $^1$H NMR (200 MHz, CDCl$_3$) δ 1.08 (9H, s, Si-t-Bu), 1.35-2.45 (6H, br m, 2'-, 5'- and 6'-H$_2$), 2.52 (2H, br m, =CH—CH$_2$), 3.88 (1H, dd, J=10.0, 5.0 Hz, 3'α-H), 4.80 and 5.17 (1H and 1H, each br s, =CH$_2$), 5.14 (1H, m, 2-H), 7.2-7.5 (16H, br m, Ar—H), 7.57 (2H, dd, J=8.0, 1.5 Hz, Ar—H), 7.68 (2H, dd, J=8.0, 1.5 Hz, Ar—H); HRMS (ESI) exact mass calculated for C$_{37}$H$_{41}$O$_2$PSiNa (M$^+$+Na) 599.2512, found 599.2534.

(h) Wittig-Horner reaction of the phosphine oxide 10 and the Grundmann ketone 11. (20S)-25-hydroxy-2-methylene-19-norvitamin D$_3$ (12). To a solution of the phosphine oxide 10 (19 mg, 29.4 µmol) in anhydrous THF (230 µL) at 0° C. was slowly added n-BuLi (2.5 M in hexanes; 12 µL, 29.7 µmol) under argon with stirring. The solution turned red. The mixture was cooled to −78° C., and precooled (−78° C.) solution of protected hydroxy ketone 11 (3 mg, 7.62 µmol) in anhydrous THF (60 µL+40 µL) was slowly added. The mixture was stirred under argon at −78° C. for 1 h and at 0° C. for 19 h. Ethyl acetate was added, and the organic layer was washed with brine, dried (MgSO$_4$) and evaporated. The residue was dissolved in hexane, applied on a silica Sep-Pak cartridge and washed with hexane/diethyl ether (98:2) to give the silylated 19-norvitamin derivative 12 (4 mg, 70%).

The product was dissolved in THF (350 µL) and tetrabutylammonium fluoride (1.0 M in THF; 318 µL, 318 µmol) was added under argon at room temperature. The stirring was continued for 18 h, brine was added and the mixture was extracted with ethyl acetate. The organic extracts were dried (MgSO$_4$) and evaporated. The residue was purified by HPLC (9.4 mm×25 cm Zorbax-Sil column, 4 mL/min) using hexane/2-propanol acetate (95:5) solvent system; 19-norvitamin 12 (1.8 mg, 85%) was collected at R$_V$=19 mL. Analytical sample of the vitamin was obtained after HPLC (9.4 mm×25 cm Zorbax Eclipse XDB-C18 column, 4 mL/min) using methanol/water (85:15) solvent system (R$_V$=44 mL).

12: UV (EtOH) λ$_{max}$ 244, 252, 261 nm; $^1$H NMR (500 MHz, CDCl$_3$) δ 0.558 (3H, s, 18-H$_3$), 0.857 (3H, d, J=6.5 Hz, 21-H$_3$), 1.217 (6H, s, 26- and 27-H$_3$), 1.95-2.05 (2H, m), 2.14 (1H, m), 2.23-2.35 (2H, m), 2.37-2.47 (2H, m), 2.59 (1H, dd, J=13.0, 4.1 Hz, 4α-H), 2.82 (1H, br dd, J~13, 4.5 Hz, 9β-H), 4.19 (1H, narr m, w/2=14 Hz, 3α-H), 4.83 and 4.96 (1H and 1H, each br s, =CH$_2$), 5.84 and 6.21 (1H and 1H, each d, J=11.3 Hz, 7- and 6-H); $^{13}$C NMR (100 MHz, CDCl$_3$) δ 12.3, 18.6, 20.9, 22.1, 23.5, 27.3, 28.8, 29.1, 29.3, 32.2, 35.4, 36.0, 40.4, 44.3, 45.7, 46.7, 56.1, 56.3, 71.1, 73.0, 107.2, 115.6, 121.4, 134.3, 142.3, 150.3; HRMS (ESI) exact mass calculated for C$_{27}$H$_{44}$O$_2$Na (M$^+$+Na) 423.3239, found 423.3253.

Example II

Preparation of (20S)-2-methylene-25-hydroxy-19-nor-vitamin D$_3$ (12, 1-desoxy-2MD) from the phosphine oxide 27.

(a) Lactonization of the quinic acid 13 (SCHEME II). (1S,3R,4R,5R)-1,3,4-Trihydroxy-6-oxa-bicyclo[3.2.1]octan-7-one (14). A solution of D-(−)-quinic acid (20.0 g, 104 mmol) and p-toluenesulfonic acid (2.2 g, 11.6 mmol) in anhydrous toluene (200 mL) and anhydrous DMF (75 mL) was refluxed under Dean-Stark trap for 34 h. The reaction mixture was cooled to 23° C. and concentrated under reduced pressure to afford a thick yellow oil. It was diluted with methylene chloride (100 mL), hexane (200 mL) was added and the resulting mixture was set aside at 23° C. for 12 h. The precipitated product was collected by vacuum filtration, and it was further dried in vacuo to afford the lactone 14 (13.0 g, 72%) as a white powder (mp 184-188° C., lit. mp 184-185° C.).

14: $^1$H NMR (500 MHz, CD$_3$OD) δ 1.87 (1H, br t, J~11 Hz, 2α-H), 2.02 (1H, ddd, J=11.7, 6.5, 2.9 Hz, 2β-H), 2.22 (1H, ddd, J=11.4, 6.0, 2.9 Hz, 8β-H), 2.47 (1H, d, J=11.4 Hz, 8α-H), 3.70 (1H, ddd, J=11.4, 6.5, 4.4 Hz, 3β-H), 3.98 (1H, br t, J~5 Hz, 4β-H), 4.70 (1H, br t, J~5 Hz, 5α-H); $^{13}$C NMR (125 MHz, CD$_3$OD) δ 37.8, 40.0, 66.8, 67.3, 73.1, 77.8, 179.5; HRMS (ESI) exact mass calculated for C$_7$H$_{10}$O$_5$Na (M$^+$+Na) 197.0426, found 197.0420.

(b) Hydroxyl groups protection in the lactone 14. (1R,2S,6R,8R)-8-Hydroxy-4-thioxo-3,5,10-trioxa-tricyclo [6.2.1.0*2,6*]undecan-9-one (15). 1,1'-Thiocarbonyldiimidazole (1.3 g, 6.86 mmol) was added to a suspension of the lactone 14 (1.08 g, 6.24 mmol) in anhydrous acetonitrile (70 mL). The mixture was stirred vigorously at room temperature for 6 h and then solvent was evaporated under reduced pressure. The residue was purified by column chromatography on silica (3% methanol/methylene chloride) to give the tricyclic compound 15 (0.84 g, 63%) as colorless crystals (mp 219-222° C.).

15: [α]$_D$ −9.7° [c 1.06, (CH$_3$)$_2$CO]; $^1$H NMR [400 MHz, (CD$_3$)$_2$CO] δ 2.24 (2H, m), 2.62 (1H, m), 2.68 (1H, ddd, J=15.2, 8.0, 2.5 Hz, 7α-H), 5.03 (1H, dd, J=5.9, 2.7 Hz, 1α-H), 5.26 (1H, m, 2β-H), 5.56 (1H, dt, J=3.1, 8.0 Hz, 6β-H); $^{13}$C NMR [100 MHz, (CD$_3$)$_2$CO] δ 35.5, 37.8, 70.7, 73.3, 77.7, 79.4, 176.8, 191.3; MS (EI) m/z (relative intensity) 216 (M$^+$, 60), 211 (15), 204 (12), 196 (42), 181 (100); exact mass calculated for C$_8$H$_8$O$_5$S 216.0092, found 216.0089.

(c) Reduction of compound 15 with tri-n-butyltin hydride. (1S,3S,5S)-1,3-Dihydroxy-6-oxa-bicyclo[3.2.1]octan-7-one (16) and (1S,4R,5R)-1,4-dihydroxy-6-oxa-bicyclo[3.2.1]octan-7-one (17). Tri-n-butyltin hydride (7.88 mL; 8.55 g, 29.40 mmol) was added by syringe pump within 75 min to a refluxing solution of compound 15 (3.18 g, 14.7 mmol) and 2,2'-azobisisobutyronitrile (0.36 g, 2.20 mmol) in anhydrous benzene/THF (3/1, 230 mL). The mixture was heated under reflux for further 3 h and then set aside for 12 h. The solvents were evaporated under reduced pressure and the residue was purified by column chromatography on silica (15→40% acetone/methylene chloride gradient) to give the diol 17 (1.94 g, 83%) as colorless crystals (mp 212-214° C.) and the isomeric compound 16 (0.11 g, 5%) as colorless crystals (mp 148-152° C.).

16: $[α]_D$ –60.3° (c 0.84, CH$_3$OH), lit $[α]_D$ –59.0° (c 0.80, CH$_3$OH); $^1$H NMR [400 MHz, (CD$_3$)2CO] δ1.48 (1H, dd, J=13.4, 10.0 Hz, 4α-H), 1.74 (1H, t, J~11 Hz, 2α-H), 2.02 (1H, d, J=11.1 Hz, 8α-H), 2.23 (1H, m), 2.34 (1H, m), 2.42 (1H, m), 3.88 (1H, m, 3β-H), 4.78 (1H, t, J~5 Hz, 5α-H); $^1$H NMR (400 MHz, CD$_3$OD) δ 1.44 (1H, dd, J=13.4, 10.1 Hz, 4α-H), 1.75 (1H, t, J~11 Hz, 2α-H), 1.97 (1H, d, J=11.2 Hz, 8α-H), 2.23 (1H, m), 2.36-2.43 (2H, m), 3.87 (1H, m, 3β-H), 4.81 (1H, t, J~5 Hz, 5α-H); $^{13}$C NMR (100 MHz, CD$_3$OD) δ 37.3, 44.3, 44.4, 65.3, 74.1, 75.9. 179.7; HRMS (ESI) exact mass calculated for C$_7$H$_{10}$O$_4$Na (M$^+$+Na) 181.0477, found 181.0482.

17: $[α]_D$ –59.7° [c 1.15, (CH$_3$)$_2$ CO]; $^1$H NMR (400 MHz, CD$_3$OD) δ 1.70 (1H, m), 1.78 (1H, m), 1.86 (1H, m), 1.97 (1H, m), 2.26 (1H, ddd, J=11.3, 6.1, 2.7 Hz, 8β-H), 2.45 (1H, d, J=11.3 Hz, 8α-H), 3.97 (1H, br t, J~4 Hz, 4β-H), 4.60 (1H, br t, J~5 Hz, 5α-H); $^1$H NMR [400 MHz, (CD$_3$)$_2$CO] δ 1.66-1.77 (2H, m), 1.84 (1H, m), 1.96 (1H, m), 2.24 (1H, ddd, J=11.2, 6.2, 2.8 Hz, 8β-H), 2.46 (1H, d, J=11.2 Hz, 8α-H), 4.00 (1H, m, 4β-H), 4.58 (1H, br t, J~5 Hz, 5α-H); $^{13}$C NMR [100 MHz, (CD$_3$)$_2$CO] δ 28.1, 30.2, 38.2, 64.4, 74.7, 77.6, 178.3; HRMS (ESI) exact mass calculated for C$_7$H$_{10}$O$_4$Na (M$^+$+Na) 181.0477, found 181.0471.

(d) Oxidation of the diol 17. (1S,5R)-1-Hydroxy-6-oxa-bicyclo[3.2.1]octane-4,7-dione (18). The mixture of alcohol 17 (2.67 g, 16.88 mmol), oven-dried activated 4 Å molecular sieves (2.7 g), pyridinium dichromate (12.90 g, 34.28 mmol) and anhydrous acetonitrile (250 mL) was stirred vigorously at room temperature for 5 h. The reaction mixture was then filtered through a pad of Celite (washed with 300 mL of ethyl acetate) and the solvents were removed under reduced pressure. Column chromatography of the residue on silica (15→40% acetone/methylene chloride gradient) afforded the ketone 18 (2.17 g, 82%) as colorless crystals (mp 144-145° C.).

18: $[α]_D$ –225° [c 1.16, (CH$_3$)$_2$CO]; $^1$H NMR (500 MHz, CD$_3$CN) δ 2.11 (2H, m, 2-H$_2$), 2.35 (1H, d, J=12.5 Hz, 8α-H), 2.46 (1H, br dd, J=16.7, ~6 Hz, 3α-H), 2.70 (1H, dt, J=16.7, ~10 Hz, 3β-H), 2.78 (1H, ddd, J=12.5, 6.8, 2.8 Hz, 8β-H), 4.51 (1H, d, J=6.8 Hz, 5α-H); $^{13}$C NMR (125 MHz, CD$_3$CN) δ 32.8, 34.0, 42.6, 74.4, 80.5, 178.0, 204.7; MS (EI) m/z 156 (M$^+$, 55), 138 (100), 100 (42), 70 (43); HRMS (EI) exact mass calculated for C$_7$H$_8$O$_4$ 156.0423, found 156.0417.

(e) Wittig reaction of the ketone 18. (1S,5R)-1-Hydroxy-4-methylene-6-oxa-bicyclo[3.2.1]octan-7-one (19). To methyl triphenylphosphonium bromide (1.78 g, 4.99 mmol) in anhydrous THF (35 mL) at 0° C. a solution of potassium tert-butoxide in THF (1.0 M; 4.74 mL, 4.74 mmol) was added dropwise. The mixture was warmed up to room temperature and stirred for additional 10 min. Ketolactone 18 (0.38 g, 2.43 mmol) in THF (10 mL) was added via cannula and stirring was continued at room temperature for next 2 h. The solvent was then removed under reduced pressure and the residue was partitioned between ethyl acetate (20 mL) and brine (40 mL). The layers were separated and the aqueous layer was extracted with ethyl acetate (5×20 mL). The organic extracts were combined, dried (MgSO$_4$), filtered and concentrated under reduced pressure. The residue was purified by column chromatography on silica (30% ethyl acetate/hexane) to give the semisolid compound 19 (0.30 g, 80%).

19: $[α]_D$ –129° (c 1.15, CHCl$_3$); $^1$H NMR (400 MHz, CDCl$_3$) δ 1.96 (2H, m), 2.05 (1H, d, J=11.3 Hz, 8α-H), 2.48 (2H, m), 2.70 (1H, ddd, J=11.3, 6.3, 2.7 Hz, 8β-H), 4.93 (1H, br s, one of =CH$_2$), 4.98 (1H, d, J=6.3 Hz, 5α-H), 5.01 (1H, d, J=1.4 Hz, one of =CH$_2$); $^{13}$C NMR (100 MHz, CDCl$_3$) δ 26.3, 33.8, 44.1, 74.4, 80.2, 112.1, 141.4, 178.7; HRMS (ESI) exact mass calculated for C$_8$H$_{10}$O$_3$Na (M$^+$+Na) 177.0528, found 177.0525.

(f) Methanolysis of the lactone 19 and hydroxyl protection. [(1S,3R)-3-[(tert-Butyldimethylsilyl)oxy]-1-hydroxy-4-methylene]cyclohexanecarboxylic acid methyl ester (20). The lactone 19 (0.88 g, 5.71 mmol) was treated with anhydrous methanol (30 mL) in a presence of activated, oven-dried 4 Å molecular sieves (0.22 g). The reaction mixture was stirred at room temperature for 48 h. Then molecular sieves were filtered out and the solvent was evaporated under reduced pressure. The crude methyl ester was dissolved in anhydrous methylene chloride (30 mL) and 2,6-lutidine (1.26 mL; 1.16 g, 10.84 mmol), cooled to –40° C. and tert-butyldimethylsilyl trifluoromethanesulfonate (1.97 mL; 2.26 g, 8.56 mmol) was added dropwise. The reaction mixture was stirred at –40° C. for 50 min. Wet methylene chloride (10 mL) was added slowly, cooling bath was removed and the reaction mixture was allowed to warm up slowly to room temperature. Then it was filtered through a pad of Celite (washed with 30 mL of methylene chloride), washed with saturated aqueous CuSO$_4$ (2×15 mL) and brine (15 mL). The organic layers were combined, dried (MgSO$_4$), filtered and concentrated under reduced pressure. The crude product was purified by column chromatography on silica (10% ethyl acetate/hexane) to afford ester 20 (1.37 g, 80%) of as a colorless oil.

20: $[α]_D$ –0.2° (c 1.05, CHCl$_3$); $^1$H NMR (500 MHz, CDCl$_3$) δ 0.07 and 0.08 (3H and 3H, each s, 2×SiCH$_3$), 0.90 (9H, s, Si-t-Bu), 1.70 (1H, m), 1.81 (2H, m), 1.97 (1H, m), 2.33 (1H, ddd, J=13.5, 4.3, 2.4 Hz, 5β-H), 2.46 (1H, dt, J=13.5, 4.3 Hz, 5α-H), 3.77 (3H, s, COOCH$_3$), 4.42 (1H, dd, J=11.1, 5.0 Hz, 3α-H), 4.80 and 5.03 (1H and 1H, each s, =CH$_2$); $^{13}$C NMR (125 MHz, CDCl$_3$) δ –5.05, –5.01, 18.3, 25.8, 29.3, 36.0, 45.3, 53.0, 69.0, 75.1, 105.7, 149.6, 176.6; HRMS (ESI) exact mass calculated for C$_{15}$H$_{28}$O$_4$SiNa (M$^+$+Na) 323.1655, found 323.1643.

(g) Reduction of the ester 20. [(1S',3R')-3'-[(tert-Butyldimethylsilyl)oxy]-1'-hydroxy-4'-methylene-cyclohexyl]methanol (21). Diisobutylaluminium hydride (1.0 M in methylene chloride; 3.83 mL, 3.83 mmol) was slowly added to a stirred solution of methyl ester 20 (0.23 g, 0.76 mmol) in methylene chloride (18 mL) at –70° C. Stirring was continued at –70° C. for 1 h and at –30° C. for 2 h. The mixture was quenched by slow addition of potassium-sodium tartrate (2 N, 4 mL), diluted with methylene chloride (200 mL), washed with brine (3×30 mL) and water (2×30 mL). Organic layer was dried (MgSO$_4$), filtered and concentrated under reduced pressure.

The residue was passed through a silica Sep-Pak cartridge (10→30% ethyl acetate/hexane gradient) to give the diol 21 (0.20 g, 94%) as colorless crystals (mp 89-90° C.).

21: $[\alpha]_D$ +1.3° (c 1.04, CHCl$_3$); $^1$H NMR (500 MHz, CDCl$_3$) δ 0.07 and 0.08 (3H and 3H, each s, 2×SiCH$_3$), 0.91 (9H, s, Si-t-Bu), 1.40 (2H, m), 1.70 (1H, m), 1.96 (1H, m), 2.33 (2H, m), 3.48 (2H, s, —CH$_2$OH), 4.40 (1H, dd, J=10.2, 5.0 Hz, 3'α-H), 4.78 and 4.97 (1H and 1H, each s, =CH$_2$); $^{13}$C NMR (125 MHz, CDCl$_3$) δ −5.0, −4.9, 18.3, 25.8, 28.9, 35.1, 44.7, 69.7, 70.7, 73.4, 105.9, 150.4; HRMS (ESI) exact mass calculated for C$_{15}$H$_{28}$O$_3$Si (M$^+$+H) 273.1886, found 273.1885.

(h) Periodate oxidation of the diol 21. (R)-3-[(tert-Butyldimethylsilyl)oxy]-4-methylene-cyclohexanone (22). To a stirred solution of diol 21 (0.76 g, 2.81 mmol) in methanol/water (5/1, 53 mL) was added sodium periodate (1.80 g, 8.43 mmol) at 0° C. Stirring was continued at 0° C. for 1 h, the reaction mixture was diluted with ethyl acetate (140 mL) and extracted with brine (3×20 mL) and water (20 mL). The combined aqueous layers were extracted with ethyl acetate (3×20 mL). The organic layers were combined and dried (MgSO$_4$), then filtered and concentrated under reduced pressure. The residue was purified on a silica Sep-Pak cartridge (5% ethyl acetate/hexane) to give the ketone 22 (0.64 g, 95%) as a colorless oil.

22: $[\alpha]_D$ −43° (c 1.25, CHCl$_3$); $^1$H NMR (400 MHz, CDCl$_3$) δ 0.03 and 0.05 (3H and 3H, each s, 2×SiCH$_3$), 0.86 (9H, s, Si-t-Bu), 2.28-2.45 (3H, m), 2.48 (1H, dd, J=14.1, 6.7 Hz, 2β-H), 2.60 (1H, dd, J=14.1, 4.2 Hz, 2α-H), 2.71 (1H, m), 4.42 (1H, m, 3β-H), 4.94 and 5.08 (1H and 1H, each s, =CH$_2$); $^{13}$C NMR (100 MHz, CDCl$_3$) δ −5.1, −5.0, 18.1, 25.6, 28.7, 41.5, 51.5, 72.7, 109.8, 147.0, 208.9; HRMS (ESI) exact mass calculated for C$_{13}$H$_{24}$O$_2$SiNa (M$^+$+Na) 263.1443, found 263.1438.

(i) Wittig reaction of the ketone 22. [(R)-3'-[(tert-Butyldimethylsilyl)oxy]-4'-methylene-cyclohexylidene]acetic acid methyl ester (mixture of 23 and 24). To a solution of ketone 22 (0.65 g, 2.38 mmol) in anhydrous benzene (20 mL) methyl(triphenylphosphoranylidene) acetate (1.59 g, 4.77 mmol) was added. The reaction mixture was heated under reflux for 15 h, then concentrated under reduced pressure and the residue was purified on a silica Sep-Pak cartridge (3→5% ethyl acetate/hexane) to afford a mixture of unsaturated esters 23 and 24 (ratio ca. 2:3; 0.63 g, 89%).

23 and 24 (mixture of isomers): $^1$H NMR (400 MHz, CDCl$_3$; selected signals) δ 0.05 and 0.07 and 0.11 (1.2H, 3H and 1.8H, each s, 2×SiCH$_3$), 0.90 (9H, s, Si-t-Bu), 3.29 (0.4H, m, 6'α-H), 3.51 (0.6H, dd, J=13.0, 4.4 Hz, 2'α-H), 4.12 (1H, m, 3'α-H), 4.80, 4.82, 5.01 and 5.03 (0.6H, 0.4H, 0.4H and 0.6H, each s, =CH$_2$), 5.68 and 5.73 (0.4H and 0.6H, s, 2-H); HRMS (ESI) exact mass calculated for C$_{16}$H$_{28}$O$_3$SiNa (M$^+$+Na) 319.1705, found 319.1710.

(j) Reduction of the esters 23 and 24. (E)- and (Z)-2-[(R)-3'-[(tert-Butyldimethylsilyl)oxy]-4'-methylene-cyclohexylidene]ethanols (25 and 26). Diisobutylaluminium hydride (1.0 M in methylene chloride; 9.89 mL, 9.89 mmol) was slowly added to a stirred solution of the mixture of the esters 23 and 24 (0.73 g, 2.47 mmol) in methylene chloride (40 mL) at −70° C. Stirring was continued at −70° C. for 2 h and −40° C. for 1 h. The mixture was quenched by slow addition of potassium-sodium tartrate (2 N, 6 mL), diluted with methylene chloride (250 mL), washed with brine (3×30 mL) and water (2×30 mL). Organic layer was dried (MgSO$_4$), filtered and concentrated under reduced pressure. The residue was purified by column chromatography on silica (10→20% ethyl acetate/hexane gradient) to give an allylic alcohol 25 (0.25 g, 39%) of as a colorless oil and the oily isomeric compound 26 (0.37 g, 58%).

25 (minor E-isomer): $[\alpha]_D$ +5.8° (c 0.98, CHCl$_3$); $^1$H NMR (400 MHz, CDCl$_3$) δ 0.06 and 0.07 (3H and 3H, each s, 2×SiCH$_3$), 0.91 (9H, s, Si-t-Bu), 1.97 (2H, m), 2.14 (1H, br t, J~11 Hz, 2'β-H), 2.47 (3H, m), 4.05 (1H, dd, J=9.8, 4.9 Hz, 3'α-H), 4.17 (2H, m, —CH$_2$OH), 4.78 and 5.01 (1H and 1H, each s, =CH$_2$), 5.46 (1H, t, J=7.0 Hz, 2-H); $^{13}$C NMR (100 MHz, CDCl$_3$) δ −5.0, −4.9, 18.3, 25.8, 29.2, 32.9, 47.3, 58.7, 7 3.2, 106.5, 123.4, 140.2, 150.0; HRMS (ESI) exact mass calculated for C$_{15}$H$_{28}$O$_2$SiNa (M$^+$+Na) 291.1756, found 291.1756.

26 (major Z-isomer): $[\alpha]_D$ −26° (c 1.09, CHCl$_3$); $^1$H NMR (500 MHz, CDCl$_3$) δ 0.06 and 0.08 (3H and 3H, each s, 2×SiCH$_3$), 0.90 (9H, s, Si-t-Bu), 2.09 (1H, dt, J=12.7, 6.6 Hz, 5'β-H), 2.17 (2H, m, 5'α- and 6'β-H), 2.27 (1H, dd, J=12.9, 7.9 Hz, 2'β-H), 2.43 (1H, dt, J=12.7, 5.8 Hz, 6'α-H), 2.50 (1H, dd, J=12.9, 4.2 Hz, 2'α-H), 4.09 (1H, m, one of —CH$_2$OH), 4.13 (1H, dd, J=7.9, 4.2 Hz, 3'α-H), 4.18 (1H, dd, J=11.9, 7.2 Hz, one of —CH$_2$OH), 4.78 and 4.96 (1H and 1H, each s, =CH$_2$), 5.60 (1H, t, J=7.2 Hz, 2-H); $^{13}$C NMR (125 MHz, CDCl$_3$) δ −4.94, −4.9, 18.3, 25.8, 33.1, 37.4, 39.0, 58.3, 73.3, 107.6, 123.7, 140.4, 149.9; HRMS (ESI) exact mass calculated for C$_{15}$H$_{28}$O$_2$SiNa (M$^+$+Na) 291.1756, found 291.1769.

(k) Preparation of the phosphine oxide 27. [(E)-[(3'R)-[(tert-Butyldimethylsilyl)oxy]-4'-methylenecyclohexylidene]ethyl]diphenylphosphine Oxide (27). To a allylic alcohol 25 (190.0 mg, 708 μmol) in anhydrous THF (5 mL) was added n-BuLi (1.6 M in hexanes; 450 μL, 125 μmol) under argon at 0° C. A solution of a freshly recrystallized tosyl chloride (141.5 mg, 743 μmol) in anhydrous THF (1.5 mL) was then added to the allylic alcohol—n-BuLi solution. The mixture was stirred at 0° C. for 5 min and set aside at 0° C. In another dry flask with air replaced by argon, n-BuLi (1.6 M in hexanes; 942 μL, 1.51 mmol) was added to diphenylphosphine (250 μL, 1.44 mmol) in anhydrous THF (2 mL) at 0° C. with stirring. The red solution was siphoned under argon pressure to the solution of tosylate until the orange color persisted. The resulting mixture was stirred for an additional 30 min at 0° C. and quenched by addition of H$_2$O (0.8 mL). Solvents were evaporated under reduced pressure, the residue was redissolved in methylene chloride (6.5 mL), and stirred with 10% H$_2$O$_2$ (3.8 mL) at 0° C. for 1 h. The organic layer was separated, washed with cold aqueous sodium sulfite (1.5 mL) and water (1.5 mL), dried (MgSO$_4$), filtered and evaporated under reduced pressure. The residue was purified on a silica Sep-Pak cartridge (5% ethyl acetate/hexane) to afford semicrystalline phosphine oxide 27 (220 mg, 69%).

27: $[\alpha]_D$ +7.9° (c 1.07, CHCl$_3$); $^1$H NMR (500 MHz, CDCl$_3$) δ 0.03 (6H, s, 2×SiCH$_3$), 0.88 (9H, s, Si-t-Bu), 1.60 (2H, m), 2.04 (1H, m, 2'β-H), 2.25 (2H, m), 2.39 (1H, dd, J=12.6, 4.8 Hz, 2'α-H), 3.12 (2H, m, =CH—CH$_2$), 3.85 (1H, dd, J=9.8, 4.8 Hz, 3'α-H), 4.70 and 4.95 (1H and 1H, each s, =CH$_2$), 5.30 (1H, ~t, J=7 Hz, 2-H), 7.25-7.5 (6H, m, Ar—H), 7.74 (4H, m, Ar—H); $^{13}$C NMR (125 MHz, CDCl$_3$) δ −5.0, 18.3, 25.8, 29.2, 30.1, 30.7, 32.4, 47.4, 73.1, 106.2, 112.2, 112.3, 128.4, 128.5, 128.51, 128.55, 131.0, 131.1, 131.2, 131.8, 141.2, 141.3, 149.9; HRMS (ESI) exact mass calculated for C$_{27}$H$_{37}$O$_2$PSiNa (M$^+$+Na) 475.2198, found 475.2208.

(l) Wittig-Horner reaction of the phosphine oxide 27 and the Grundmann ketone 11. (20S)-25-hydroxy-2-methylene-19-norvitamin D$_3$ (12). To a stirred solution of 27 (49 mg, 108 μmol) in anhydrous THF (800 μL) 2 drops of phenyl lithium solution (1.8 M in di-n-butyl ether) were added at −20° C.

until the solution became deep orange. Then 54 µL (97 µmol) of the of phenyl lithium solution was added dropwise. After 20 min the reaction mixture was cooled to −78° C. and the precooled (−78° C.) solution of ketone 11 (28 mg, 71 µmol) in anhydrous THF (400 µL+100 µL) was added via cannula. The mixture was stirred for 2 h at −78° C. and at 0° C. for 4 h. Ethyl acetate (30 mL) was added and the organic phase was washed with brine (7 mL), dried (MgSO$_4$), filtered and concentrated under reduced pressure. The residue was purified on a silica Sep-Pak cartridge (0→2% ethyl acetate/hexane) to give protected 19-norvitamin D derivative.

To a stirred solution of the obtained oily compound (11 mg, 17 µmol) in methanol (2 mL) (1S)-(+)-10-camphorsulfonic acid (7 mg, 30 µmol) was added at 0° C. Then cooling bath was removed and the reaction mixture was stirred overnight at room temperature. A few drops of saturated aqueous solution of sodium bicarbonate and water (3 mL) was added and the mixture was extracted with ethyl acetate (5×7 mL). The combined organic phases were dried (MgSO$_4$), concentrated under reduced pressure and the residue was purified on a silica Sep-Pak cartridge (10% ethyl acetate/hexane) as well as by HPLC (9.4 mm×25 cm Zorbax Rx-Sil column, 4 mL/min) using 7% hexane/2-propanol solvent system ($R_V$=21 mL). Further purification was achieved by HPLC (9.4 mm×25 cm Zorbax Eclipse XDB-C18 column, 4 mL/min) using methanol/water (85:15) solvent system ($R_V$=44 mL). Analytically pure 19-norvitamin D$_3$ analog 12 (6.9 mg, 14% yield from 11) was obtained, identical in all respects with the compound described in the EXAMPLE I.

SCHEME I and SCHEME II are set forth below.

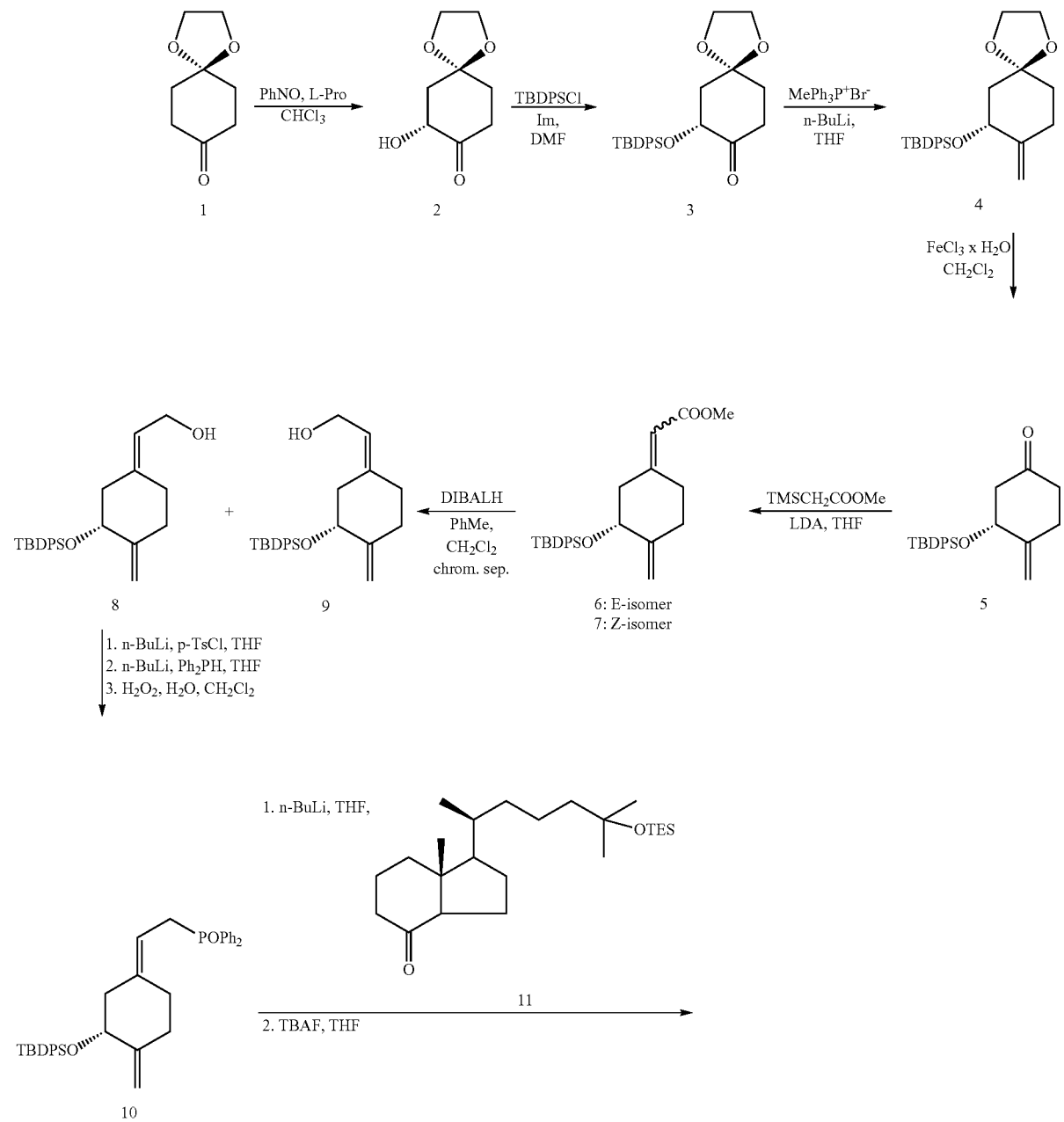

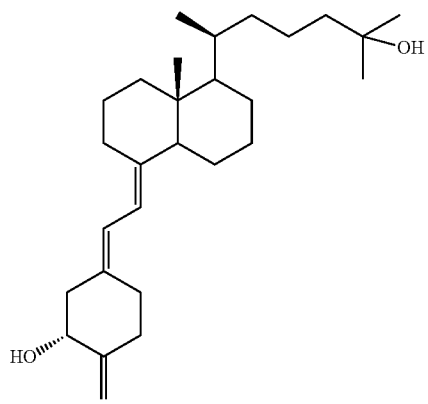
SCHEME 2
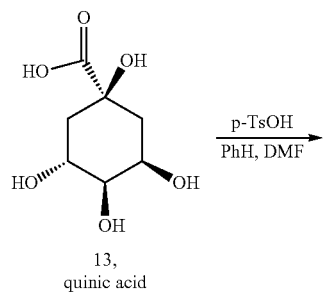
13,
quinic acid
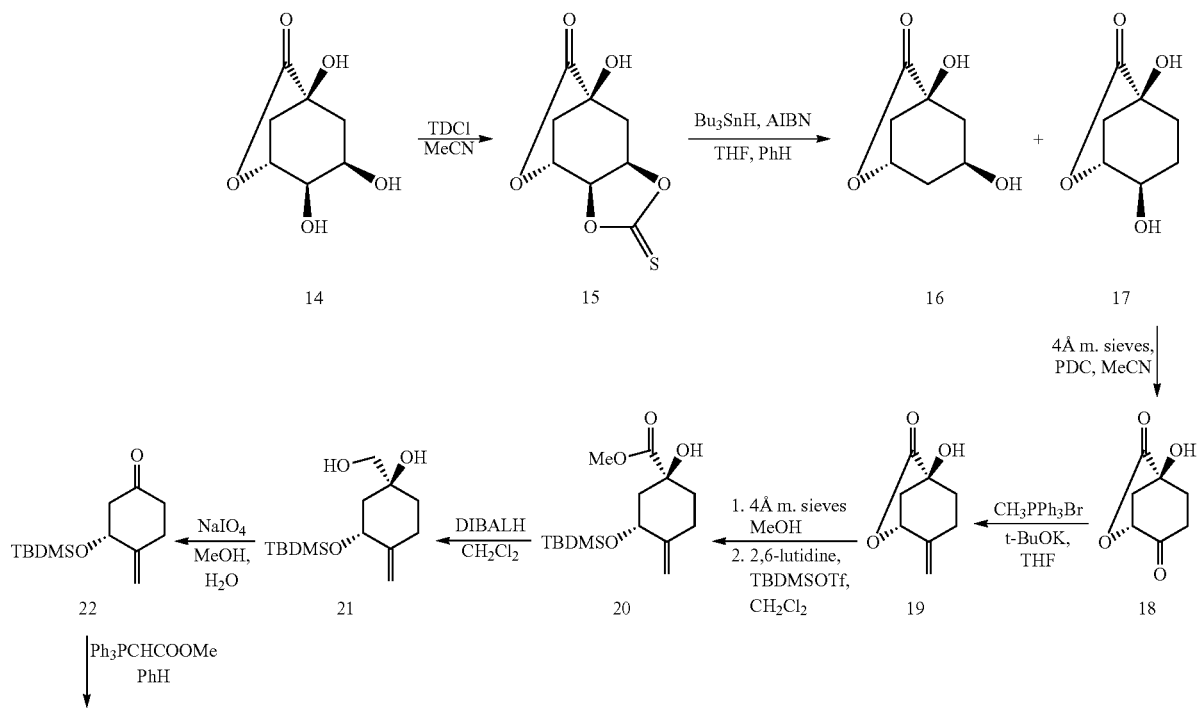

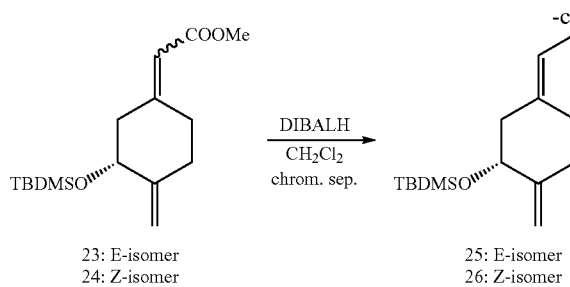
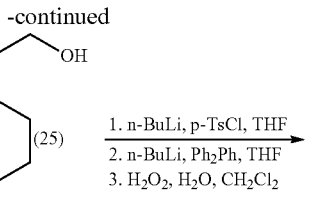

23: E-isomer
24: Z-isomer

25: E-isomer
26: Z-isomer

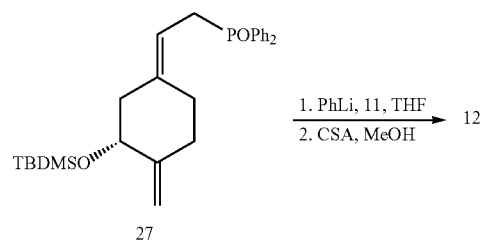

27

Biological Activity of (20S)-25-Hydroxy-1-Desoxy-2-Methylene-19-Norvitamin $D_3$ The introduction of a methylene group to the 2-position, the removal of the methylene substituent at carbon 10, and orienting the methyl group at carbon 20 in its epi or S configuration had little or no effect on binding to the full length recombinant rat vitamin D receptor, as compared to 1α,25-dihydroxyvitamin $D_3$. The compound 1-desoxy-2MD bound with only slightly less affinity to the receptor as compared to the standard 1,25-$(OH)_2D_3$ (FIG. 1). It might be expected from these results that compound 1-desoxy-2MD would have equivalent biological activity. Surprisingly, however, compound 1-desoxy-2MD is a highly selective analog with unique biological activity.

Figure 5A:
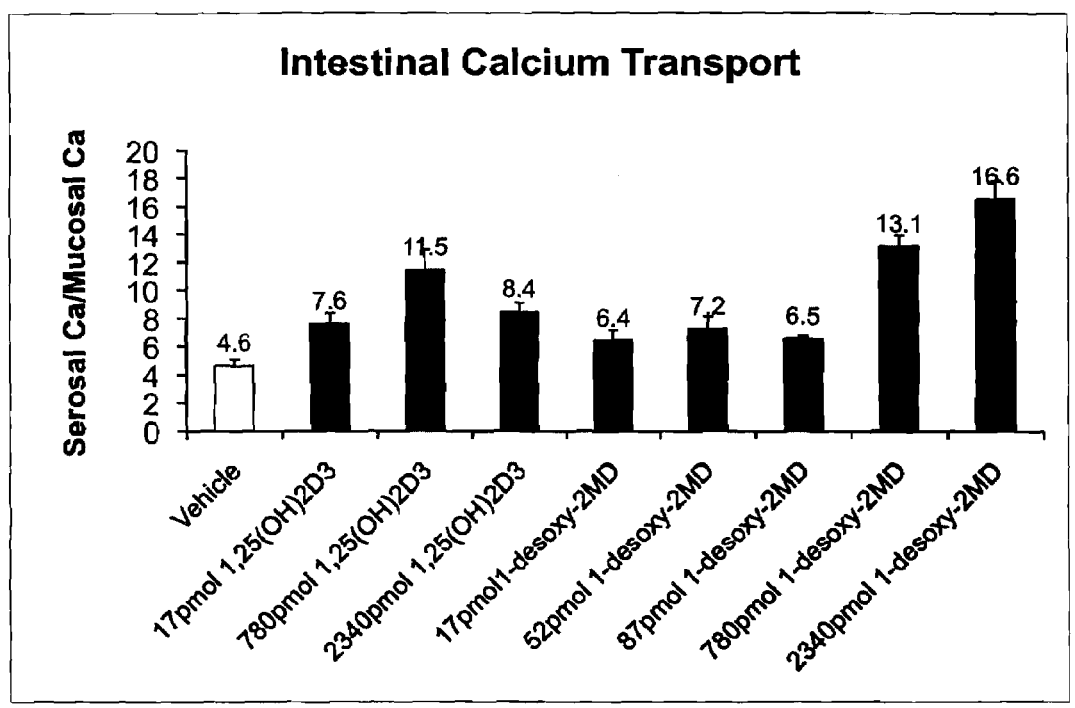
FIGS. 5A and 5B are bar graphs illustrating the intestinal calcium transport activity of 1,25(OH)$_2$D$_3$ as compared to 1-desoxy-2MD.
Figure 5B:
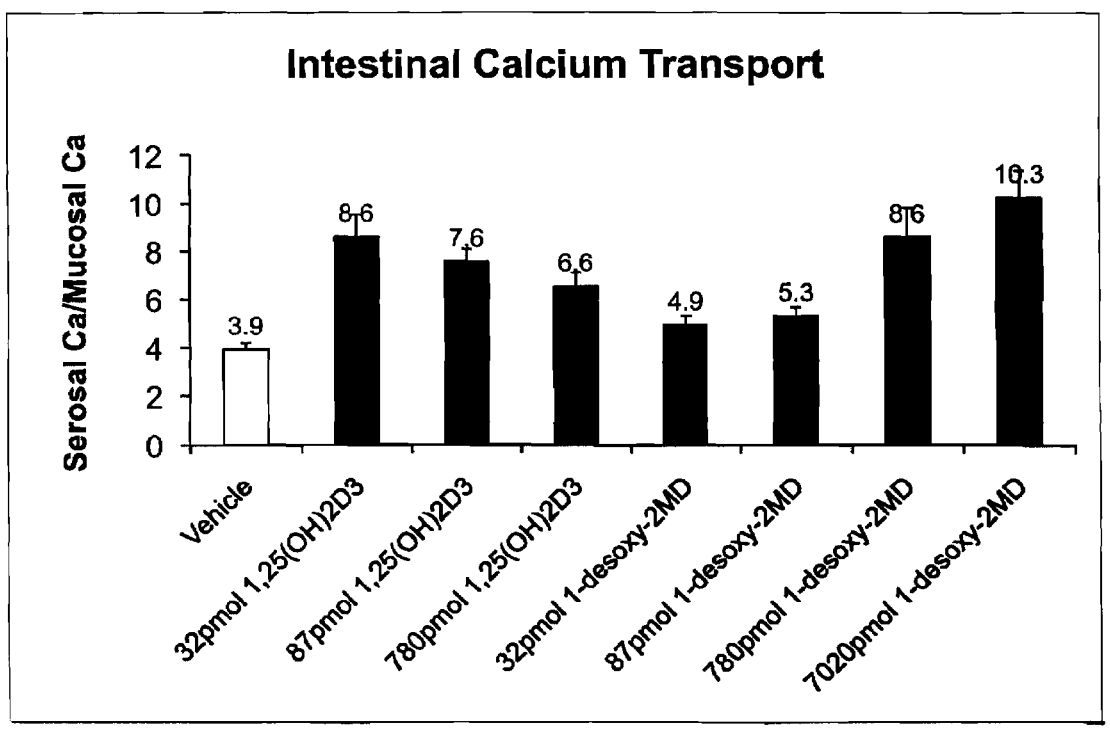

FIGS. 5A and 5B show that 1-desoxy-2MD has relatively low activity as compared to that of 1,25-dihydroxyvitamin $D_3$ (1,25$(OH)_2D_3$), the natural hormone, in stimulating intestinal calcium transport. 1-desoxy-2MD is about 20 times less potent than 1,25$(OH)_2D_3$ in promoting active calcium transport across the gut.

Figure 4A:
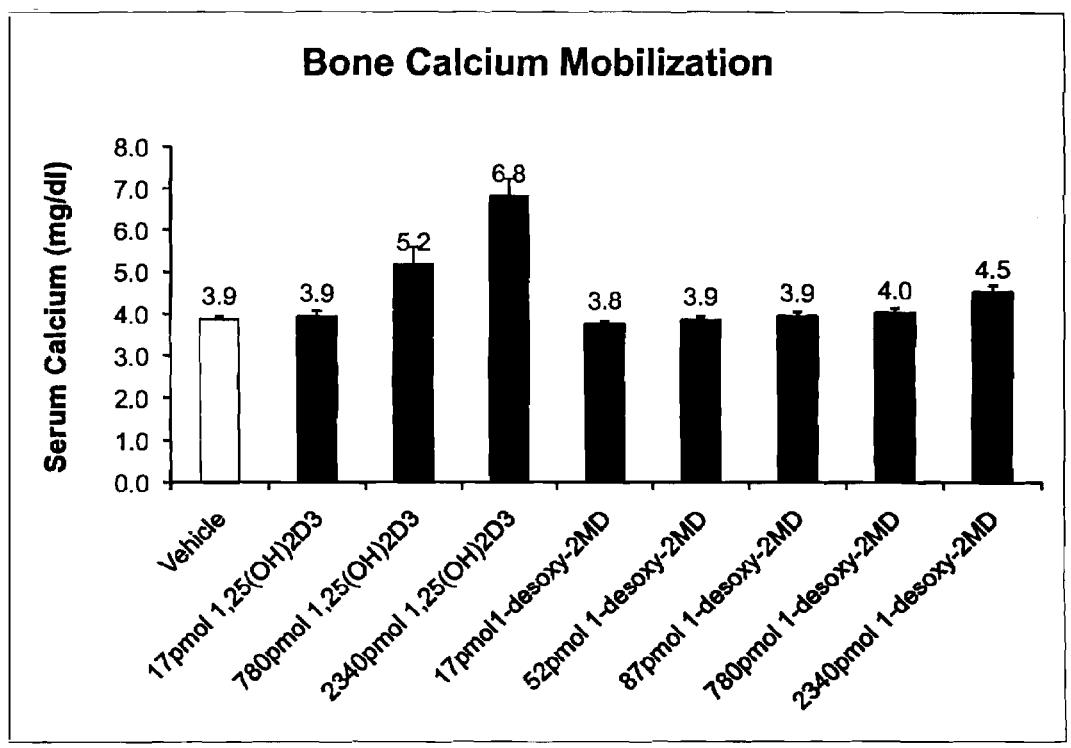
FIGS. 4A and 4B are bar graphs illustrating the bone calcium mobilization activity of 1,25(OH)$_2$D$_3$ as compared to 1-desoxy-2MD.
Figure 4B:
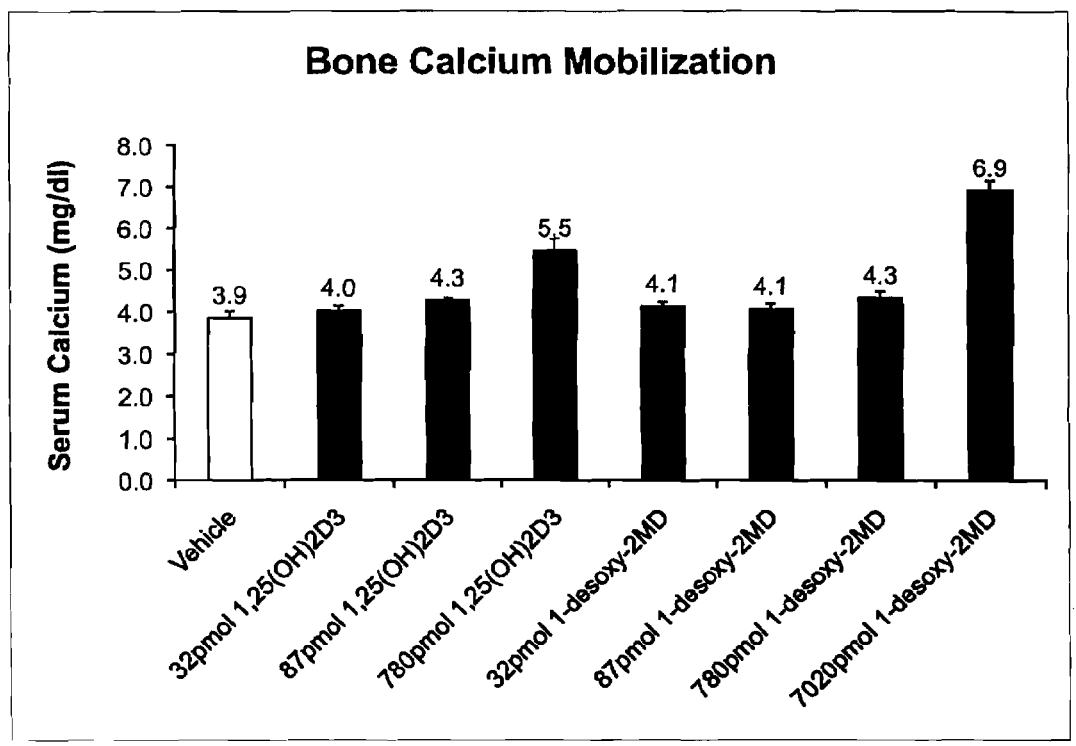

FIGS. 4A and 4B demonstrate that 1-desoxy-2MD has relatively low bone calcium mobilization activity, as compared to 1,25$(OH)_2D_3$. 1-desoxy-2MD is less potent than the native hormone in releasing bone calcium stores as little to no activity is observed until 7020 pmol/rat is administered; whereas, significant increases in serum calcium are observed at 780 pmol when the native hormone is given.

FIGS. 4-5 thus illustrate that 1-desoxy-2MD may be characterized as having relatively low calcemic activity.

Figure 2:
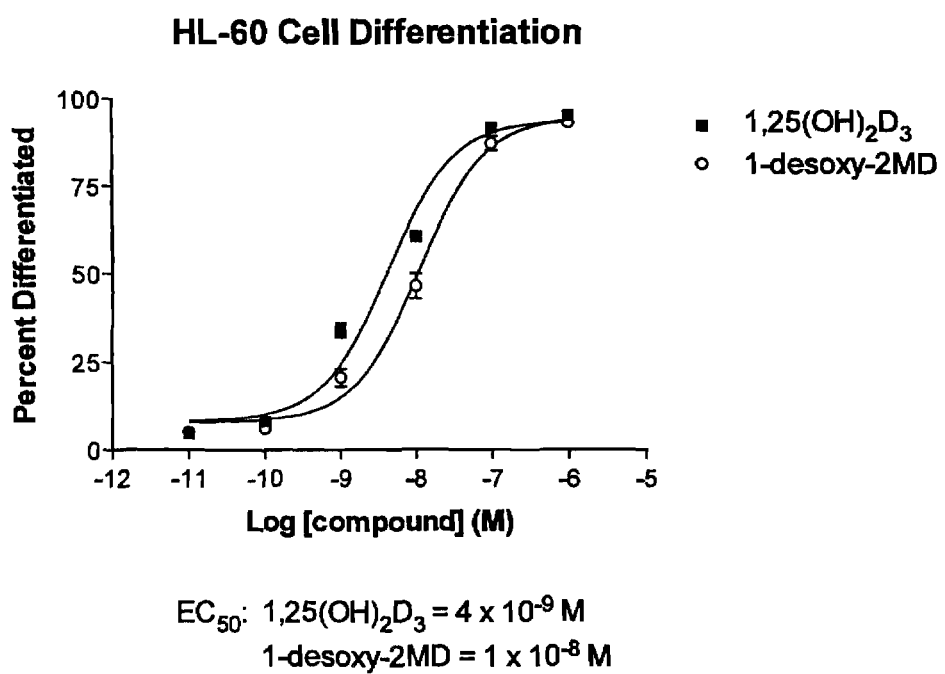

FIG. 2 illustrates that 1-desoxy-2MD is almost as potent as 1,25$(OH)_2D_3$ on HL-60 cell differentiation, making it an excellent candidate for the treatment of a cancer, especially for the prevention or treatment of leukemia, colon cancer, breast cancer, skin cancer and prostate cancer.

Figure 3:
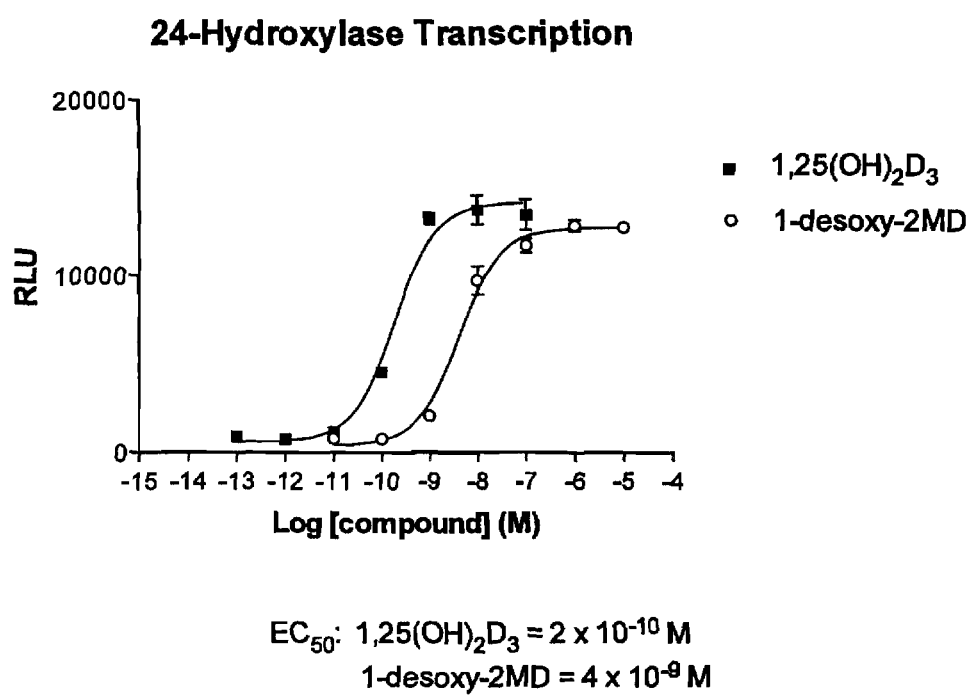

FIG. 3 illustrates that the compound 1-desoxy-2MD has less transcriptional activity than 1α,25-dihydroxyvitamin $D_3$ in bone cells. In bone cells, 1-desoxy-2MD is about 20 times less potent than 1,25$(OH)_2D_3$ in increasing transcription of the 24-hydroxylase gene. This result, together with the cell differentiation activity of FIG. 2, suggests that 1-desoxy-2MD will be very effective in treating the above referred to cancers because it has direct cellular activity in causing cell differentiation, gene transcription, and in suppressing cell growth.

Experimental Methods

The compounds of the invention were prepared and studied using the following methods.

Vitamin D Receptor Binding

Test Material
Protein Source
Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration was optimized such that no more than 20% of the added radiolabeled ligand was bound to the receptor.

Study Drugs
Unlabeled ligands were dissolved in ethanol and the concentrations determined using UV spectrophotometry (1,25 $(OH)_2D_3$: molar extinction coefficient=18,200 and $\lambda_{max}$=265 nm). Radiolabeled ligand ($^3$H-1,25$(OH)_2D_3$, ~159 Ci/mmole) was added in ethanol at a final concentration of 1 nM.

Assay Conditions
Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs
The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.
Cells
Human promyelocytic leukemia (HL60) cells were grown in RPMI-1640 medium containing 10% fetal bovine serum. The cells were incubated at 37° C. in the presence of 5% $CO_2$.
Assay Conditions
HL60 cells were plated at $1.2\times10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (Suda et al, J. Nutr. 100:1049, 1970) (0.47% Ca)+vitamins AEK for one week followed by Diet 11 (0.02% Ca)+vitamins AEK for 3 weeks. The rats were then switched to the same diet containing 0.47% Ca for one week followed by two weeks on the same diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Interpretation of Data

VDR binding, HL60 cell differentiation, and transcription activity. 1-desoxy-2MD ($K_i=1\times10^{-10}$M) has slightly less activity than the natural hormone 1α,25-dihydroxyvitamin $D_3$ ($K_i=5\times10^{-11}$M) in its ability to compete with [$^3$H]-1,25(OH)$_2$D$_3$ for binding to the full-length recombinant rat vitamin D receptor (FIG. 1). 1-desoxy-2MD is also a little less potent ($EC_{50}=1\times10^{-8}$M) in its ability (efficacy or potency) to promote HL60 differentiation as compared to 1α,25-dihydroxyvitamin $D_3$ ($EC_{50}=4\times10^{-9}$M) (See FIG. 2). Also, compound 1-desoxy-2MD ($EC_{50}=4\times10^{-9}$M) has about 20 times less transcriptional activity in bone cells than 1α,25-dihydroxyvitamin $D_3$ ($EC_{50}=2\times10^{-10}$M) (See FIG. 3). These data also indicate that 1-desoxy-2MD will have significant activity as an anti-cancer agent, especially for preventing or treating leukemia, colon cancer, breast cancer, skin cancer and prostate cancer because it has direct cellular activity in causing cell differentiation and in suppressing cell growth.

Calcium mobilization from bone and intestinal calcium absorption in vitamin D-deficient animals. Using vitamin D-deficient rats on a low calcium diet (0.02%), the activities of 1-desoxy-2MD and 1,25(OH)$_2$D$_3$ in intestine and bone were tested. As expected, the native hormone (1,25(OH)$_2$D$_3$) increased serum calcium levels at the dosages tested (FIGS. 4A and 4B). FIGS. 4A and 4B also show that 1-desoxy-2MD has significantly less activity in mobilizing calcium from bone than 1,25(OH)$_2$D$_3$. Administration of 1-desoxy-2MD at 780 pmol/day for 4 consecutive days resulted in little or no mobilization of bone calcium. 1-desoxy-2MD is less potent than the native hormone in releasing bone calcium stores as little to no activity is observed until 7020 pmol/rat is administered; whereas, significant increases in serum calcium are observed at 780 pmol when the native hormone is given.

Intestinal calcium transport was evaluated in the same groups of animals using the everted gut sac method (FIGS. 5A and 5B). These results show that the compound 1-desoxy-2MD is about 20 times less potent in promoting intestinal calcium transport activity when administered at the recommended lower dosages, as compared to 1,25(OH)$_2$D$_3$. Thus, it may be concluded that 1-desoxy-2MD has low intestinal calcium transport activity at the tested doses.

These results further illustrate that 1-desoxy-2MD is an excellent candidate for numerous human therapies as described herein. 1-desoxy-2MD is an excellent candidate for treating a cancer because: (1) it has significant VDR binding, transcription activity and cellular differentiation activity; (2) it has low risk of hypercalcemic liability unlike 1,25(OH)$_2$D$_3$; and (3) it is easily synthesized.

For prevention and/or treatment purposes, the compounds of this invention defined by formula I and Ia may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly 1-desoxy-2MD of formula Ia, may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly 1-desoxy-2MD, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly 1-desoxy-2MD, as defined by the above formula I and Ia as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually or parenterally in dosages of from about 0.01 μg/day to about 1000 μg /day, and preferably from about 0.1 μg/day to about 500 μg/day.

The compounds I, particularly 1-desoxy-2MD, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly 1-desoxy-2MD, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:
1. A compound having the formula:

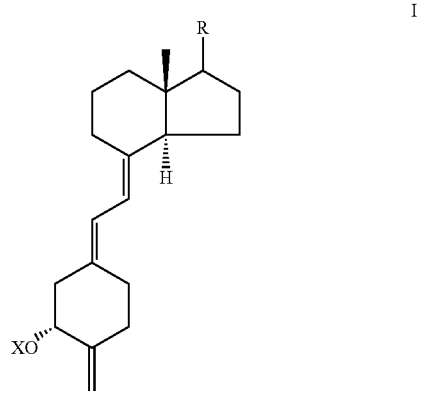

where X is selected from the group consisting of hydrogen and a hydroxy-protecting group, and where R may he an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

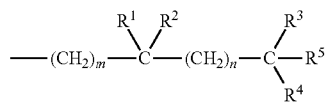

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of, R$^2$, R$^3$, and R$^4$, independently, is selected from deuterium, deuteroalkyl, hydrogen, fluoro, tnfluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R⁵ represents hydrogen, hydroxy, protected hydroxy, or $C_{1-5}$ alkyl and wherein any of the CH—groups at positions 20, 22, or 23 in the side chain may he replaced by a nitrogen atom, or where any of the groups —CH(CH₃)—,—(CH₂)$_m$—, —CR₁R₂— or—(CH₂)$_n$—at positions 20, 22, and 23, respectively, may be replaced by an oxygen or sulfur atom.

2. The compound of claim 1 wherein X is hydrogen.

3. The compound of claim 1 wherein R is selected from:

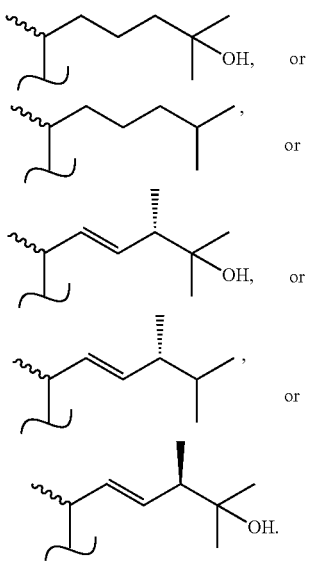

4. The compound of claim 3 wherein X is hydrogen.

5. A pharmaceutical composition containing an effective amount of at least one compound as claimed in claim 1 together with a pharmaceutically acceptable excipient.

6. The pharmaceutical composition of claim 5 wherein said effective amount comprises from about 0.01 µg to about 1000 µg per gram of composition.

7. The pharmaceutical composition of claim 5 wherein said effective amount comprises from about 0.1 µg to about 500 µg per gram of composition.

8. A compound having the formula:

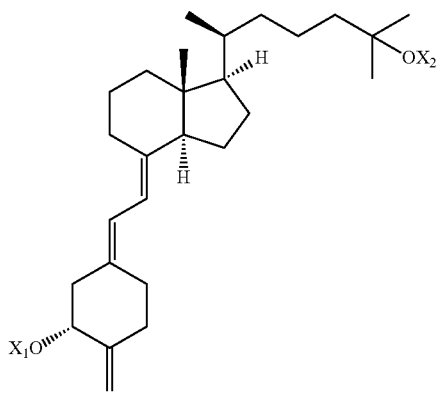

where $X_1$ and $X_2$, which may be the same or different, are each selected from hydrogen or a hydroxy-protecting group.

9. The compound of claim 8 wherein $X_2$ is hydrogen.

10. The compound of claim 8 wherein $X_1$ is hydrogen.

11. The compound of claim 8 wherein $X_1$ and $X_2$ are both t-butyldimethylsilyl.

12. A pharmaceutical composition containing an effective amount of at least one compound as claimed in claim 8 together with a pharmaceutically acceptable excipient.

13. The pharmaceutical composition of claim 12 wherein said effective amount comprises from about 0.01 µg to about 1000 µg per gram of composition.

14. The pharmaceutical composition of claim 12 wherein said effective amount comprise from about 0.1 µg to about 500 µg per gram of composition.

15. A compound having the formula:

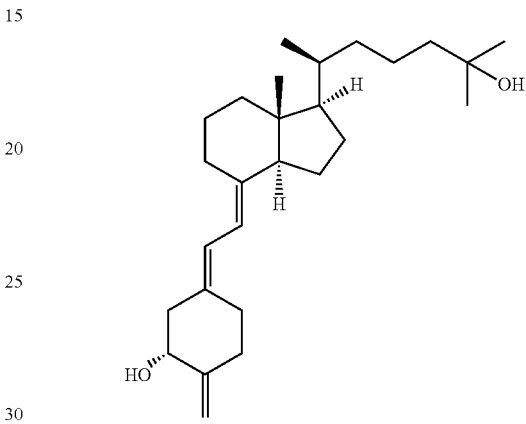

and named (20S)-25-hydroxy-1-desoxy-2-methylene-19-norvitamin $D_3$.

16. A pharmaceutical composition containing an effective amount of (20S)-25-hydroxy-1-desoxy-2-methylene-19-norvitamin $D_3$ together with a pharmaceutically acceptable excipient.

17. The pharmaceutical composition of claim 16 wherein said effective amount comprises from about 0.01 µg to about 1000 µg per gram of composition.

18. The pharmaceutical composition of claim 16 wherein said effective amount comprises from about 0.01 µg to about 500 µg per gram of composition.

19. A method of treating a disease selected from the group consisting of leukemia, colon cancer, breast cancer, skin cancer or prostate cancer comprising administering to a subject with said disease an effective amount of a 1-desoxy -2-methylene-19-nor-vitamin D compound having the formula:

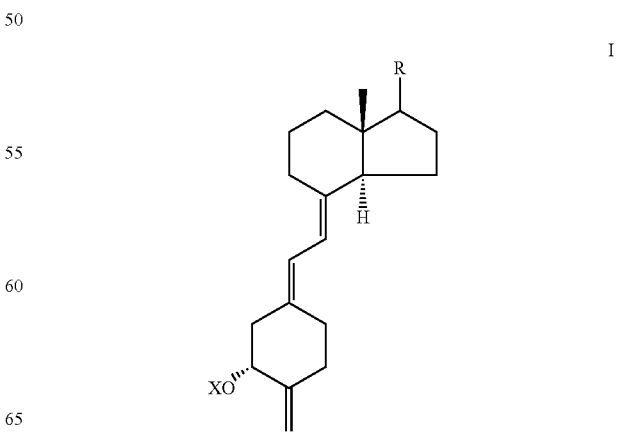

where X is selected from the group consisting of hydrogen and a hydroxy-protecting group, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

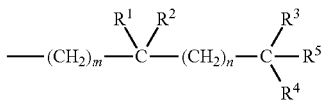

where m and n, independently, represent the integers from 0 to 5, where R$^1$ is selected from hydrogen, deuterium, hydroxy, protected hydroxy, tluoro, trifluaromethyl, and C$_{1-5}$-alkyl, which may be straight chain or branched and, optionally, bear a hydroxy or protected-hydroxy substituent, and where each of R$^2$,R$^3$,and R$^4$, independently, is selected, from deuterium, deuteroalkyl, hydrogen, fluoro, trifluoromethyl and C$_{1-5}$ alkyl, which may be straight-chain or branched, and optionally, bear hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$,or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH—groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

20. The method of claim 19 wherein the vitamin D compound is administered orally.

21. The method of claim 19 wherein the vitamin D compound is administered parenterally.

22. The method of claim 19 wherein the vitamin D compound is administered transdermally.

23. The method of claim 19 wherein the compound is administered rectally.

24. The method of claim 19 wherein the compound is administered nasally.

25. The method of claim 19 wherein the compound is administered sublingually.

26. The method of claim 19 wherein the vitamin D compound is administered in a dosage of from shoot 0.01 µg/day to about 1000 µg/day.

27. The method of claim 19 wherein the vitamin D compound has the formula:

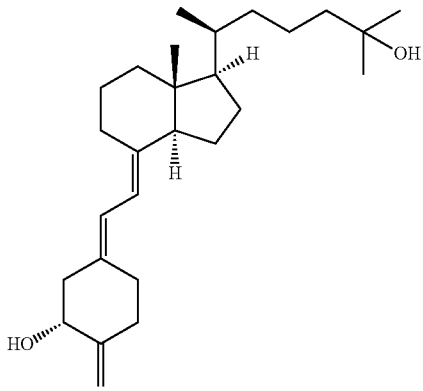 [SMILES: C=C1CC/C(=C\C=C2/CCC[C@]3(C)[C@@H]([C@@H](C)CCCC(C)(C)O)CC[C@@H]23)C[C@H]1O]

and is named (20S)-25-hydroxy-i-desosy-2-methylene-19-norvitamin D$_3$.

28. (20R)-25-hydroxy-1-desoxy-2-methylene-19-nor-vitamin D$_3$ having the formula:

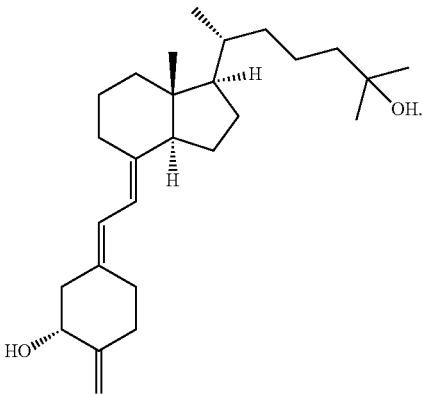 [SMILES: C=C1CC/C(=C\C=C2/CCC[C@]3(C)[C@@H]([C@H](C)CCCC(C)(C)O)CC[C@@H]23)C[C@H]1O]

29. A pharmaceutical composition containing an effective amount of (20R)-25-hydroxy-1-desoxy-2-methylene-19-nor-vitamin D$_3$ together with a pharmaceutically acceptable excipient.

30. The pharmaceutical composition of claim 29 wherein said effective amount comprises from about 0.01 µg to about 1000 µg per gram of composition.

31. The pharmaceutical composition of claim 29 wherein said effective amount comprises from about 0.1 µg to about 500 µg per gram of composition.

* * * * *